(12) United States Patent
Chern et al.

(10) Patent No.: US 8,173,693 B2
(45) Date of Patent: May 8, 2012

(54) BENZENESULFONAMIDE DERIVATIVES AND PHARMACEUTICAL COMPOSITION THEREOF

(75) Inventors: Ji-Wang Chern, Taipei (TW); Grace Shiahuy Chen, Fengyuan (TW); Pei-Teh Chang, Taipei (TW); Kuan-Yu Chen, Guanyin Township, Taoyuan County (TW); Meng-Ling Chen, Keelung (TW); Hsueh-Yun Lee, Linkou Township, Taipei County (TW); Chiung Hua Huang, Taipei (TW); Chun-Tang Chiou, Taipei (TW)

(73) Assignee: Purzer Pharmaceutical Co., Ltd., Taipei (TW)

( * ) Notice: Subject to any disclaimer, the term of this patent is extended or adjusted under 35 U.S.C. 154(b) by 0 days.

(21) Appl. No.: 12/929,883

(22) Filed: Feb. 23, 2011

(65) Prior Publication Data
US 2011/0230651 A1 Sep. 22, 2011

(30) Foreign Application Priority Data
Mar. 16, 2010 (TW) ................. 99107557 A

(51) Int. Cl.
*C07D 209/40* (2006.01)
*C07D 409/02* (2006.01)
*A61K 31/404* (2006.01)
(52) U.S. Cl. ......... 514/415; 514/422; 548/483; 548/467
(58) Field of Classification Search .................. None
See application file for complete search history.

(56) References Cited

U.S. PATENT DOCUMENTS
5,854,274 A * 12/1998 Yoshino et al. ............... 514/290

FOREIGN PATENT DOCUMENTS
JP 2002-167376 * 6/2002

OTHER PUBLICATIONS

Owa, Takashi et al., "Discovery of Novel Antitumor Sulfonamides Targeting GI Phase of the Cell Cycle", Journal of Medicinal Chemistry, 42, 3789-3799, 1999.*
Owa, Takashi et al., "A Focused Compound Library of Novel N-(7-Indolylbenzenesulfonamides for the Discovery of Potent Cell Cycle Inhibitors", Bioorganic and Medicinal Chemistry Letters, 10, 1223-1226, 2000.*
Derwent Abstract of JP 2002-167376, Jun. 2002.*

* cited by examiner

*Primary Examiner* — Kamal A Saeed
*Assistant Examiner* — Michael Barker
(74) *Attorney, Agent, or Firm* — Bacon & Thomas, PLLC

(57) ABSTRACT

The present invention is related to derivatives of benzenesulfonamide represented by formula (I), and the pharmaceutical composition thereof. In addition, the benzenesulfonamide derivatives disclosed in the present invention can serve as potential cell cycle inhibitors, and thereby these benzenesulfonamide derivatives and the pharmaceutical composition thereof can be antitumor drug candidates, which might aim at cell cycle. Particularly, the benzenesulfonamide derivatives disclosed in the present invention may function as antitumor drugs to treat solid cancers.

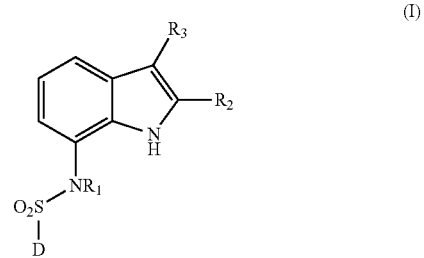

18 Claims, 3 Drawing Sheets

BENZENESULFONAMIDE DERIVATIVES AND PHARMACEUTICAL COMPOSITION THEREOF

BACKGROUND OF THE INVENTION

1. Field of the Invention

The present invention relates to benzenesulfonamide derivatives and a pharmaceutical composition thereof and, more particularly, to benzenesulfonamide derivatives used as a cell-cycle inhibitor for treating solid tumors and a pharmaceutical composition thereof.

2. Description of Related Art

In the recent years, it is found that foods or food additives, and environmental pollutions are blamed for directly causing cancer. In addition, tobacco smoke is also a powerful carcinogen causing the deaths of millions. Hence, not only in Taiwan, but also in the developed countries around the whole world, the incidence rates of cancers are quite high. According to the data published by the American Cancer Society, cancer is perhaps the most significant threat to public health. In addition, according to the data published by Department of Health in Taiwan, cancer is the first among the 10 leading causes of death since 1982. Solid tumors of lung cancer, liver cancer, and colorectal cancer are the most common tumors causing death, and the death rate of these cancers is about 50% of all cancer deaths. Recently, anti-cancer drugs of etoposide and cisplatin have been developed, which are effective in the treatment of leukemia and lymph cancer. However, the curative effect of these drugs on lung cancer, liver cancer, and colorectal cancer is not good enough.

Currently, a surgical operation can be performed to cut the cancer cell and partial lymph gland to treat the solid tumors such as gastric cancer. Also, some other treatments such as radiotherapy, chemotherapy, and immune therapy have been developed to treat cancers. In the recent years, the development of several therapeutic agents has lead to treatment cancers through new anti-cancer mechanisms, and it has been proved that the survival rate of patients can be increased by treating them with these therapeutic agents. These therapeutic agents can treat tumor cells through inhibiting cell cycle progression, angiogenesis, farnesyl transferase, and tyrosine kinases. Recently, the therapeutic agent for inhibiting the cell cycle progression, such as wortmannin, 5-fluorouracil, daunomycin, and colchicines are the most potential anti-cancer drugs.

Eisai Co., Ltd. has investigated two kinds of benzenesulfonamide derivatives, which have already entered clinical trials. The formulas of these two benzenefulfonamide derivatives are represented as follow:

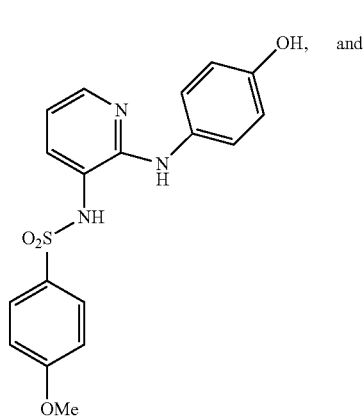

E7010

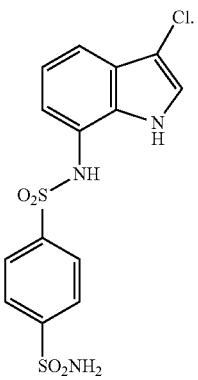

E7070

These two benzenesulfonamide derivatives are inhibitors of the cell cycle, and cause cell death. E7010 shows great effect on the test for anti-cancer activity in mice, and has already entered phase II clinic trials. In addition, E7070 has the best anti-cancer activity among the benzenesulfonamide derivatives, and has already entered phase II clinic trials. It has been proved that E7070 can inhibit human colon cancer cell (colon 38), and the $IC_{50}$ of E7070 is 0.26 μM (Owa et. al., J. Med. Chem. 1999, 42, 3789-3799). However, although these benzenesulfonamide derivatives have already entered clinical trials, whether these therapeutic agents can be used in the cancer treatment is still unknown.

Several therapeutic agents have been applied on the treatment of solid tumors. However, not all of them are effective due to different locations of tumor cells, different patients, and side effects generated therefrom. Because cancer is the first among the 10 leading causes of death, and solid tumors are the most common tumors causing death, it is urgent to investigate therapeutic agents for inhibiting solid tumor cells. Hence, there is a long unfulfilled need for the present invention which provides a new compound for treating solid tumors, and inhibiting the growth of the tumor cells.

SUMMARY OF THE INVENTION

The object of the present invention is to provide benzenesulfonamide derivatives, which can inhibit the growth of solid tumors, and exhibit great effects on treating tumor cells of gastric cancer, liver cancer, colorectal cancer, and nasopharyngeal cancer.

To achieve the object, the benzenesulfonamide derivative of the present invention is represented by the following formula (I):

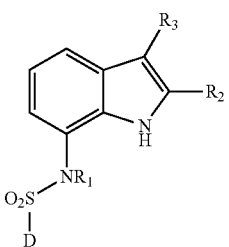

(I)

wherein,
$R_1$ is H, or $C_{1-6}$ alkyl;
$R_2$ and $R_3$ are each independently H,

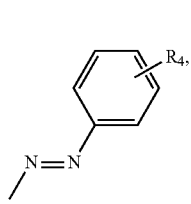

or bond together to form

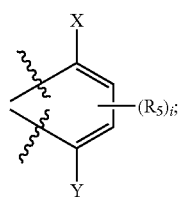

D is

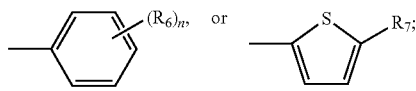

$R_4$ is H, or nitro;
X, Y, and each $R_5$ are each independently H, or $C_{1-6}$ alkyl;
each $R_6$ is independently H, halogen, $C_{1-6}$ alkyl, $C_{1-6}$ alkoxy, $C_{1-6}$ alkyl substituted with halogen, $C_{1-6}$ alkoxy substituted with halogen, nitro, —$NR_8R_9$, or —$SO_2NR_{10}R_{11}$;
$R_7$ is H, or halogen;
$R_8$, $R_9$, $R_{10}$, and $R_{11}$ are each independently H, or $C_{1-6}$ alkyl; and
i, and n are each independently 0, 1, 2, or 3.

According to the benzenesulfonamide derivative of the present invention, preferably, $R_8$, $R_9$, $R_{10}$, and $R_{11}$ is H. Also, preferably, $R_1$ is H, or $C_{1-3}$ alkyl. More preferably, $R_1$ is, methyl, ethyl, propyl, or iso-propyl.

According to one aspect of the present invention, $R_1$ may be H, or $C_{1-3}$ alkyl, D may be

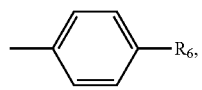

and $R_6$ may be H, halogen, $C_{1-6}$ alkyl, $C_{1-6}$ alkoxy, nitro, —$NH_2$, or —$SO_2NH_2$. In this aspect, $R_6$ is H, Cl, methyl, methoxy, nitro, —$NH_2$, or —$SO_2NH_2$, preferably. In addition, $R_2$ and $R_3$ bond together to form

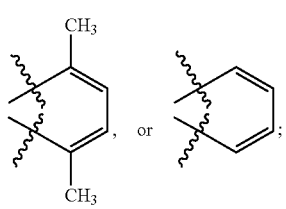

$R_2$ and $R_3$ are H; or $R_2$ is H, and $R_3$ is

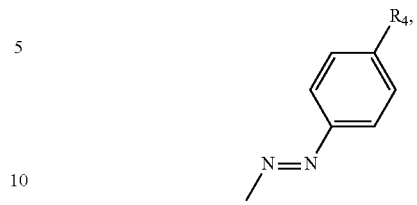

preferably.

According to another aspect of the present invention, $R_1$ may be H, or $C_{1-3}$ alkyl, D may be

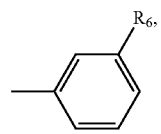

and $R_6$ may be H, $C_{1-6}$ alkyl substituted with halogen, or $C_{1-6}$ alkoxy substituted with halogen. In this aspect, $R_6$ is —$CF_3$, preferably. In addition, $R_2$ and $R_3$ bond together to form

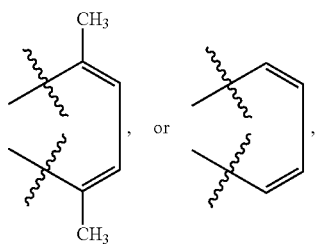

preferably.

According to a further aspect of the present invention, $R_1$ may be H, D may be

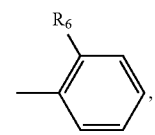

and $R_6$ may be H, halogen, $C_{1-6}$ alkyl, $C_{1-6}$ alkoxy, nitro, —$NH_2$, or —$SO_2NH_2$. In this aspect, $R_6$ is nitro, preferably. In addition, $R_2$ and $R_3$ bond together to form

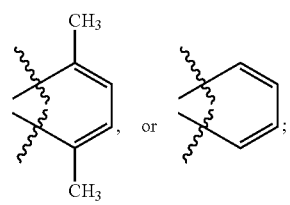

or $R_2$ and $R_3$ are H, preferably.

According to further another aspect of the present invention, $R_1$ may be H, or $C_{1-3}$ alkyl, D may be

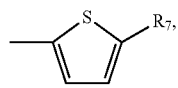

and $R_7$ may be H, or halogen. In this aspect, $R_1$ is H, or methyl, and $R_7$ is Cl, preferably. Also, $R_2$ and $R_3$ bond together to form

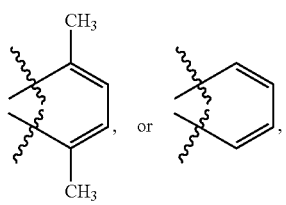

preferably.

The term of "alkyl" refers to a non-aromatic hydrocarbon group with a straight chain or a branch chain.

The term of "alkoxy" refers to an alkyl linked to oxygen.

The term of "halogen" refers to a halogen group comprising F, Cl, Br, or I.

The benzenesulfonamide derivative of the present invention may be used as an inhibitor of the cell cycle, and has effect on the treatment of solid tumors. In addition, the benzenesulfonamide derivative of the present invention further has effect on the treatment of turner cells such as gastric cancer cells, liver cancer cells, colorectal cancer cells, and nasopharyngeal cancer cells.

Furthermore, another object of the present invention is to provide a pharmaceutical composition used as a cell-cycle inhibitor, which may comprise an effective amount of a benzenesulfonamide derivative represented by the following formula (I), a salt thereof, or a pro-drug thereof. The pharmaceutical composition of the present invention may further comprise other pharmaceutically acceptable additives such as eluents, carriers, and excipients, in order to increase the effect on the treatment of cancer.

The term of "treating" refers to administration of one or more of the benzenesulfonamide derivatives represented by the formula (I) to a subject, who suffers from the aforementioned cancers, to achieve the purpose of curing, relieving, altering, ameliorating, or improving the symptom.

The term of "an effective amount" refers to the amount of one or more of the benzenesulfonamide derivatives, a salt thereof, or a pro-drug thereof, which is required to confer the desired effect on the subject. Effective amounts depend upon therapeutic agents, route of administration, types of cancer, and age and weight of patients.

The pharmaceutical composition containing the benzenesulfonamide derivatives represented by the formula (I) can be administered parenterally, orally, nasally, rectally, topically, or buccally.

A pharmaceutical composition for oral administration can be any orally acceptable dosage form including, but not limited to, capsules, tablets, emulsions, suspensions, dispersions, and solutions. The tablets may comprise any commonly used carriers such as lactose and cornstarch. In addition, lubricating agents, such as magnesium stearate, may also be used in the tablets. When the pharmaceutical composition is orally administered in a form of capsules, useful diluents may be lactose and dried cornstarch. When the pharmaceutical composition is orally administered in a form of aqueous suspensions or emulsions, some active additives can be suspended or dissolved in an oily phase by use of emulsifying or suspending agents. If it is desired, sweetening, flavoring, or coloring agents can be added into the pharmaceutical composition of the present invention.

The term of "parenterally" refers to subcutaneous, intracutaneous, intravenous, intramuscular, intraarticular, intraarterial, intrasynovial, intrasternal, intrathecal, intralesional, intracranial injection, or other infusion techniques. A sterile injectable composition can be a solution or suspension containing a non-toxic and pharmaceutically acceptable diluent or solvent, such as 1,3-butanediol. The pharmaceutically acceptable diluent or solvent can be mannitol, water, Ringer's solution, and isotonic solution of NaCl. In addition, oil with low volatility may also be used as a solvent or a suspension, such as mono- or diglycerides. Fatty acid, such as oleic acid and its glyceride derivatives, may also be used in the preparation of an injectable composition. Especially, olive oil and castor oil are natural pharmaceutically acceptable oils. Furthermore, other suitable diluents, dispersants, carboxymethyl cellulose, or similar dispersing agents may also be used with the solvent or the suspension. Some surfactants such as Tweens or Spans, similar emulsifying agents, or bioavailable enhancers, which are commonly used in the manufacture of pharmaceutically acceptable solid, liquid, or other dosage forms, may also be used in the pharmaceutical composition of the present invention.

An inhalation composition can be prepared according to the conventional formulation in the art. For example, the inhalation composition can be prepared as a solution of saline. In addition, preservatives such as benzyl alcohol, absorption promoters for increasing bioavailability, fluorocarbons, or/and other dispersion agents known in the art can be added into the inhalation composition of the pharmaceutical composition of the present invention.

The carrier used in the pharmaceutical composition must be "acceptable", which means that the carrier is compatible with the active ingredient of the composition and non-toxic to the subject to be treated. One or more stabilizers can be used as an excipient for the delivery of the benzenesulfonamide derivatives of the present invention. Examples of the carriers may comprise: silicon oxide, magnesium stearate, cellulose, sodium lauryl sulfate, and D&C Yellow #10.

DETAILED DESCRIPTION OF THE PREFERRED EMBODIMENT

Figure 1:
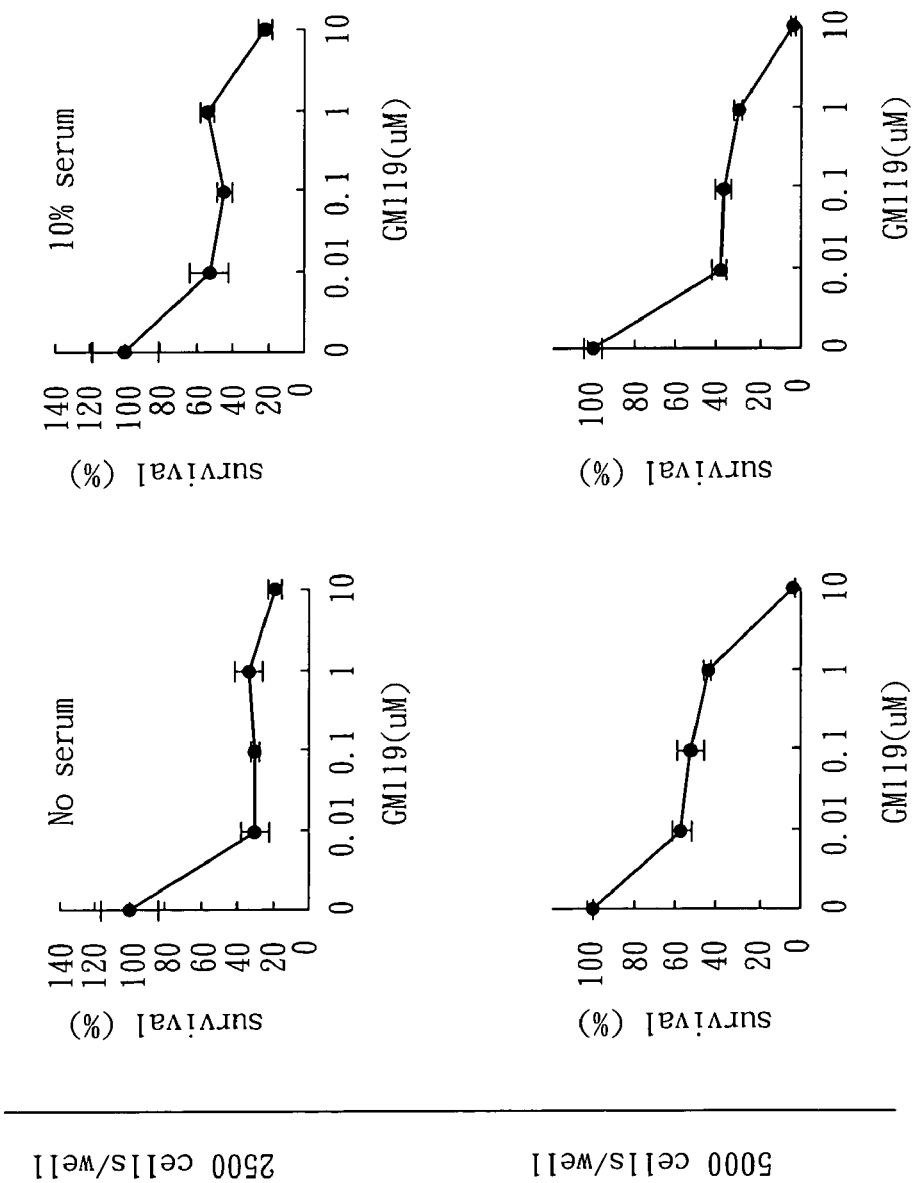
FIG. 1 is a result of an in vitro assay showing that GM119 of the present invention kills the murine mammary carcinoma 4T1 cell.

The synthesis mechanism of the benzenesulfonamide derivatives of the present invention is represented by the following Scheme I.

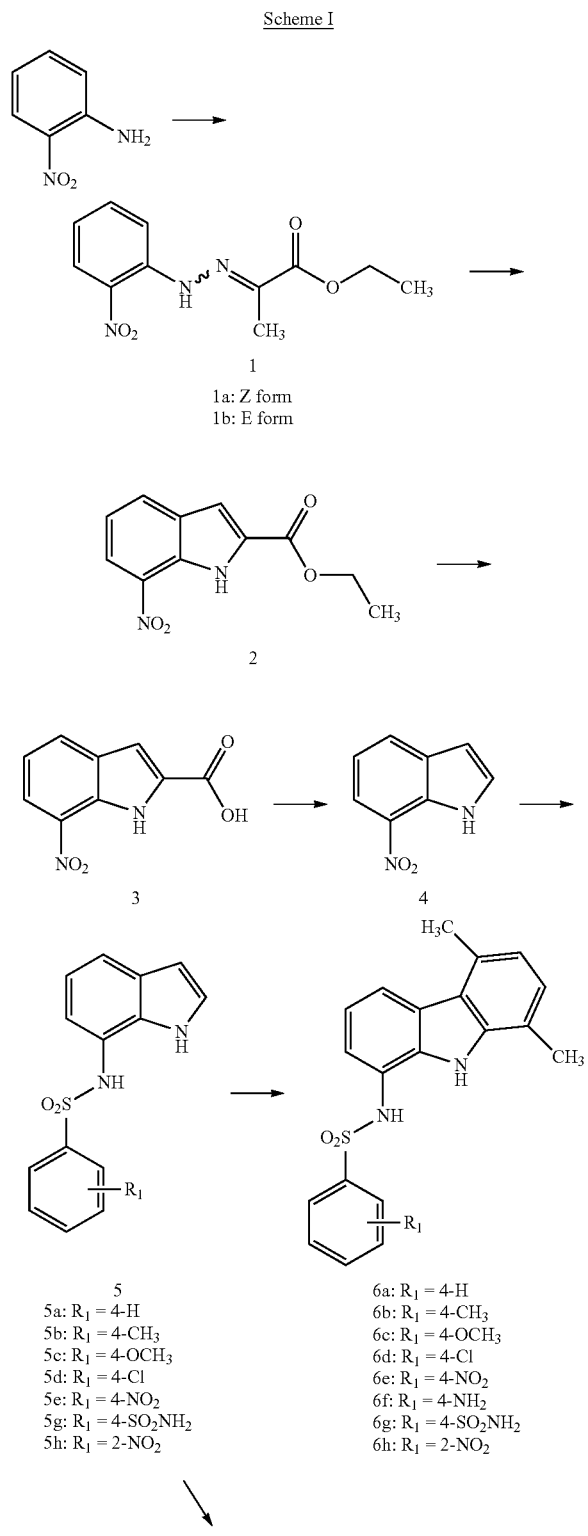

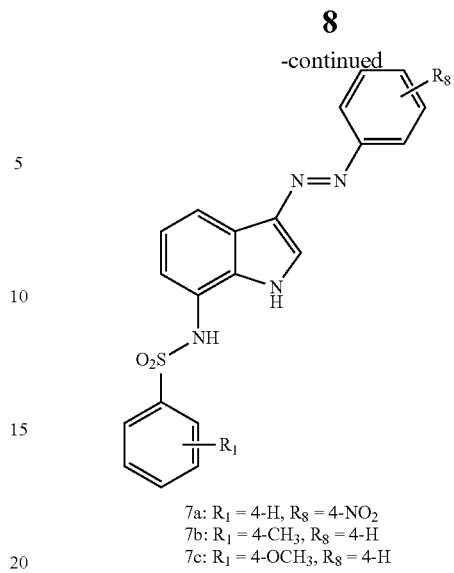

7a: $R_1$ = 4-H, $R_8$ = 4-$NO_2$
7b: $R_1$ = 4-$CH_3$, $R_8$ = 4-H
7c: $R_1$ = 4-$OCH_3$, $R_8$ = 4-H

The following methods and instruments are used to analyze the synthesized compounds of the present invention.

Determination of the melting point (mp): The melting points of the compounds are determined by the Melting Point Apparatus (Box 6402, HOLLISTON, Mass. 01740-6402. USA) manufactured by Laboratory Devices, INC. USA.

NMR analysis: The $^1H$ and $^{13}C$ NMR spectrums of the compounds are analyzed by the Brucker AMX-400 spectrometer or Brucker DPX-200 spectrometer, and the chemical shift is represented by ppm (δ).

Mass spectrum determination: In the present invention, the mass spectra are divided into low-resolution and high-resolution spectra. The low-resolution spectra are determined by use of Gas-Liquid Chromatography Mass Spectrometer (GLC-MS) (JEOL JMS-SX102A) through electron impact ionization. The high-resolution spectra are determined by use of High Performance Liquid Chromatograph (HPLC-MS) (MAT-95XL FIRMS) through electron impact ionization.

Element analysis: The determinations of the elements of C, H, and N in the compounds are performed by use of Haraeus CHN—O Rapid Elemental Analyzer, and the allowable error is ±0.4%.

Thin-layer chromatography (TLC): The compounds are developed by a TLC plate coated with silica gel (Kieselgel 60F254, Merck), and UV light is irradiated on the TLC plate to make sure the reaction is completed.

Column Chromatography: The purification is performed by use of a silica column (Merck Kieselgel 60 230-400 or 70-230 mesh).

Embodiment 1

Preparation of Compound 5a
(N-(1H-Indol-7-yl)-benzenesulfonamide))

Example 1

Preparation of Compounds 1a and 1b (Ethyl Pyruvate o-nitrophenylhydrazone)

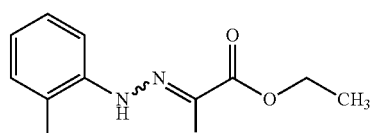

1a: Z form
1b: E form

A solution of diazonium salt was prepared under ice bath by the following steps. First, 2-nitroaniline (25.47 g, 0.18 mmol) was added into water (64.6 mL), mixed with $HCl_q$ (76.4 mL), and stirred for 10 min. Then, a solution of $NaNO_2$ (13.3.7 g) in water (50 mL) are added drop by drop into the solution. During the addition of the solution of $NaNO_2$, bubbles were generated. When the solution was stirred and became clear, the color of the solution was tawny, and no bubbles were generated. On the other hand, 2-methyl-3-oxobutyric acid ethyl ester (26.10 g, 0.14 mmol) was dissolved in ethanol (191 mL) under ice bath, a solution of $KOH_{aq}$ (50%) with 32.47 g of KOH was slowly added therein, cold water (380 mL) was added therein, and the resulting solution was stirred for 10 min. Then, the solution of diazonium salt was added into the resulting solution. When these two solutions were mixed, a yellow solid was formed. The mixed solution was filtered after stirring for 10 min. The yellow solid was washed by water until the filtrate was neutral by using a litmus test. Then, the product was re-crystallized in ethanol to obtain a needle-shaped yellow solid 1 (30.00 g, 85%), which was a mixture with Z form (compound 1a) and E form (compound 1b).

1a: mp 93-94° C. (lit. 94-95.5° C.);
$^1$H NMR (200 MHz, $CDCl_3$) δ1.38 (t, J=7.0 Hz, 3H, $CH_3$), 2.24 (s, 3H, $CH_3$), 4.37 (q, J=7.2 Hz, 2H, $CH_2$), 6.92 (t, J=7.2 Hz, ArH, 1H), 7.54 (t, J=7.2 Hz, 1H, ArH), 8.18 (dd, J=1.4, 7.2 Hz, 1H, ArH), 8.18 (d, J=7.2 Hz, 1H, ArH), 13.85 (s, 1H, NH);
$^{13}$C NMR (50 MHz, $CDCl_3$) δ10.9, 14.8, 62.0, 116.8, 120.5, 122.6, 130.1, 130.6, 131.1, 131.4, 133.9, 161.2;
MS (EI) m/z 252 (M+1, 100%), 251 (M$^+$, 84%), 136 (M−115, 58%).

1b: mp 113-114° C. (lit. 117-118° C.);
$^1$H NMR (200 MHz, $CDCl_3$) δ1.37 (t, J=7.0 Hz, 3H, $CH_3$), 2.21 (s, 3H, $CH_3$), 4.33 (q, J=7.2 Hz, 2H, $CH_2$), 6.96 (dt, J=1.2, 7.7 Hz, ArH, 1H), 7.58 (t, J=7.2 Hz, ArH, 1H), 8.00 (d, J=8.6 Hz, ArH, 1H), 8.15 (dd, J=1.4, 8.6 Hz, ArH, 1H), 10.91 (s, 1H, NH);
$^{13}$C NMR (100 MHz, $CDCl_3$) δ11.6, 14.2, 61.6, 116.8, 120.2, 125.7, 132.7, 136.2, 139.2, 140.6, 164.5;
MS (EI) m/z 251 (M$^+$, 100%), 43 (M−208, 63%).

Example 2

Preparation of Compound 2 (Ethyl 7-nitro-1H-indole-2-carboxylate)

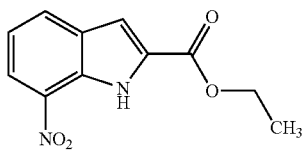

The dried compounds 1a and 1b (12.00 g, 47.76 mmol) were added into a three-necked flask (250 mL), and then polyphosphoric acid (64.56 g, 191.05 mmol) was added therein. The solution was heated to 70° C., mixed well, and then heated to 80° C. After 12 hours, the reaction was completed by checking with TLC. Before the solution was cooled, the sticked black solution was poured into cold water (400 g). The resulting solution was stirred until the polyphosphoric acid was fully hydrolyzed. The color of the resulting solution was black, and a brown-black solid was formed. Then, the resulting solution was filtered, and the brown-black solid was dried. The brown-black solid was extracted with petroleum ether (bp 60-90° C.) by a Solex extraction for 12 hr. After the extraction, the petroleum ether solution was concentrated to obtain a yellow solid. The yellow solid was re-crystallized in ethanol to obtain a needle-shaped yellow solid, compound 2 (10.5 g, 94%).

mp 92-93° C. (lit. 91-93° C.);
$^1$H NMR (200 MHz, $CDCl_3$) δ1.41 (t, J=7.2 Hz, 3H, $CH_3$), 4.42 (q, J=7.2 Hz, 2H, $CH_2$), 7.20 (t, J=7.9 Hz, 1H, ArH), 7.28 (d, J=2.1 Hz, 1H, ArH), 7.97 (d, J=7.8 Hz, 1H, ArH), 8.21 (d, J=8.0 Hz, 1H, ArH), 10.25 (s, 1H, NH);
$^{13}$C NMR (50 MHz, $CDCl_3$) δ14.8, 62.0, 109.7, 120.5, 122.6, 130.0 130.6, 131.1, 131.3, 133.8, 161.1;
MS (EI) m/z 235 (M+1, 100%), 234 (M$^+$, 69%), 189 (M−45, 38%).

Example 3

Preparation of Compound 3 (7-Nitro-1H-indole-2-carboxylic acid)

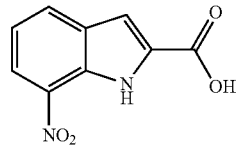

The compound 2 (13.79 g, 58.88 mmol) was added into a flask (250 mL), ethanol (72.7 mL, 40° C.) was added into the flask, and the solution was stirred for 5 min. Then, a solution of KOH formulated with KOH (7.25 g, 189.59 mmol) and water (17.40 g) was added into the solution, and the solution was stirred for 5 min to obtain a clear solution with red oxide color. When the solution was cooled down, a yellow-brown solid was started to precipitate. After the solution was stirred for 3 hr, hot water (295 mL) was added to dissolve the yellow-brown solids to obtain a clear solution with red oxide color. Then, 3 N of HCl was added into the solution, and a breast-yellow solid was precipitated. The solution was kept stirring unitl the precipitation of the yellow solids was stopped, and filtered. The yellow solids were washed by water, dried, and re-crystallized in ethanol to obtain a fiber-shaped light-yellow solid, compound 3 (11.57 g, 96%).

mp 269-271° C. (lit. 269-272° C.);
$^1$H NMR (200 MHz, DMSO-d6) δ7.35 (t, J=8.0 Hz, 1H, ArH), 7.40 (d, J=2.0 Hz, 1H, ArH), 8.22 (d, J=7.8 Hz, 1H, ArH), 8.27 (dd, J=0.8, 8.0 Hz, 1H, ArH), 11.16 (s, 1H, NH);
$^{13}$C NMR (50 MHz, acetone-d$_6$) δ109.6, 110.0, 120.6, 122.3, 130.1, 131.3, 131.8, 134.0, 161.6;
MS (EI) m/z 206 (M$^+$, 100%), 188 (M−18, 65%), 142 (M−64, 49%), 114 (M−92, 43%).

Example 4

Preparation of Compound 4 (7-Nitro-1H-indole)

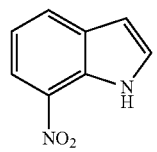

The compound 3 (1.63 g, 7.91 mmol) was dissolved in quinoline (13 mL), and then CuO (0.19 g) was added therein. The mixture was stirred and heated to 194° C. During the heating process, gas was generated. After 2 hr, there was no gas generated, the reaction was completed, and the TLC test was used to confirm the completion of the reaction. Then, the solution was poured into an HCl solution formulated by HCl (21.3 mL) and cold water (42.6 mL), and black precipitates were formed after stirring. The resulting solution was filtered, and the black precipitates and the filtrate were extracted by ether. Both phases of the extraction was collected, and respectively washed with saturated $NaHCO_3$ solution and water. After dehydration by $Na_2SO_4$, the organic layer was filtered and concentrated to obtain a yellow solid. Then, the yellow solid was re-crystallized in EtOH to obtain a needle-shaped light-yellow solid, compound 4 (0.87 g, 69%).

mp 96-97° C. (lit. 95-96° C.);

$^1$H NMR (200 MHz, $CDCl_3$) δ6.63 (dd, J=2.2, 1.0 Hz, 1H, ArH), 7.08-7.18 (m, 1H, ArH), 7.32 (t, J=3.0 Hz, 1H, ArH), 7.90 (d, J=7.8 Hz, 1H, ArH), 8.08 (d, J=8.1 Hz, 1H, ArH), 9.88 (s, 1H, NH);

$^{13}$C NMR (50 MHz, acetone-$d_6$) δ103.7, 118.9, 119.2, 128.4, 129.1, 129.3, 132.9, 133.5;

MS (EI) m/z 162 ($M^+$, 100%), 116 (M−46, 87%), 104 (M−58, 41%), 89 (M−73, 53%).

Example 5

Preparation of Compound 5a
(N-(1H-Indol-7-yl)benzenesulfonamide)

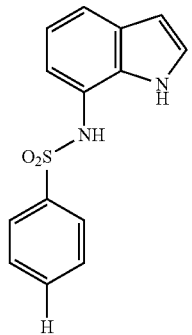

The compound 4 (1.44 g, 8.88 mmol) was dissolved in isopropanol (25 mL), and then Fe powder (1.50 g, 26.86 mmol) and an $NH_4Cl$ solution formulated with $NH_4Cl$ (0.10 g, 1.87 mmol) and water (4 mL) were added. The resulting solution was stirred and heated to 60° C. After heating for 2 hr, a TLC test was used to confirm the completion of the reaction. Then, active charcoal was added into the reaction solution, and stirred for 3 min. The solution was filtered, and ethyl acetate was used to wash the residue until the volume of the filtrate was 100 mL. Then, benzenesulfonyl chloride (1.90 g, 10.76 mmol) and pyridine (4.0 mL, 49.68 mmol) was added into the solution. The resulting solution was stirred at room temperature for 10 hr, and a TLC test was used to confirm the completion of the reaction. After the reaction was completed, ethyl acetate was added to dilute the reaction solution to 200 mL. Then, the reaction solution was sequentially washed with 1 N of HCl, water, saturated $NaHCO_3$ solution, and brine. The color of the organic layer was red oxide after the washing steps. $Na_2SO_4$ was used for dehydration, and the organic layer was filtered and concentrated to obtain a solid. The solid was re-crystallized in ethanol to obtain a needle-shaped white solid, compound 5a (2.28 g, 94%).

mp 178-179° C.;

$^1$H NMR (200 MHz, $CDCl_3$) δ6.41 (d, J=7.4 Hz, 1H, ArH), 6.54 (dd, J=2.2, 3.1 Hz, 1H, ArH), 6.86 (t, J=7.8 Hz, 1H, ArH), 6.90 (s, 1H, NH), 7.24-7.26 (m, 2H, ArH), 7.31-7.32 (m, 1H, ArH), 7.34-7.36 (m, 1H, ArH), 7.50 (d, J=8.0 Hz, 1H, ArH), 7.54-7.59 (m, 2H, ArH), 9.20 (s, 1H, NH);

$^{13}$C NMR (50 MHz, $CDCl_3$) δ103.2, 118.5, 120.2, 120.3, 120.4, 125.8, 127.9, 129.5, 130.6, 132.4, 133.7, 138.3;

MS (EI) m/z 272 ($M^+$, 63%), 131 (M−141, 100%), 104 (M−168, 94%), 77 (M−195, 85%);

HRMS (m/z) for $C_{14}H_{12}N_2O_2S(M^+)$: Calcd, 272.0620. Found, 272.0617.

Anal. ($C_{14}H_{12}N_2O_2S$): Calcd, C, 61.75; H, 4.44; N, 10.29. Found, C, 61.48; H, 4.52; N, 10.22.

Embodiment 2

Preparation of Compound 5b
(N-(1H-Indol-7-yl)-4-methylbenzenesulfonamide)

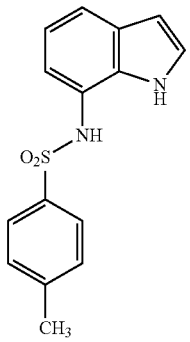

The compound 4 of the Embodiment 1 (2.00 g, 12.33 mmol) was dissolved in isopropanol (25 mL), and then Fe powder (2.07 g, 37.06 mmol) and an $NH_4Cl$ solution formulated with $NH_4Cl$ (0.13 g, 2.43 mmol) and water (7 mL) were added. After the resulting solution was heated at 60° C. for 3.5 hr, a TLC test was used to confirm the completion of the reaction. Then, active charcoal was added into the reaction solution, and stirred for 3 min. The solution was filtered, and ethyl acetate was used to wash the residue until the volume of the filtrate was 100 mL. A solution formulated with 4-methylbenzenesulfonyl chloride (3.29 g, 17.26 mmol) and pyridine (3.00 mL, 37.27 mmol) was added into the solution. The resulting solution was stirred at room temperature for 3 hr, and a TLC test was used to confirm the completion of the reaction. After the reaction was completed, ethyl acetate was added to dilute the reaction solution to 250 mL. Then, the reaction solution was sequentially washed with 1 N of HCl, water, saturated $NaHCO_3$ solution, and brine. The color of the organic layer was red oxide after the washing step. $Na_2SO_4$ was added for dehydration, and the organic layer was filtered and concentrated to obtain a solid. The solid was re-crystallized in ethanol to obtain a needle-shaped white solid, compound 5b (2.27 g, 64%).

mp 159-160° C. (lit. 157-159° C.);

$^1$H NMR (200 MHz, acetone-$d_6$) δ2.34 (s, 1H, $CH_3$), 6.47 (dd, J=3.1, 2.0 Hz, 1H, ArH), 6.73 (dd, J=7.6, 1.2 Hz, 1H, ArH), 6.84 (dt, J=7.6, 1.6 Hz, 1H, ArH), 7.26 (dd, J=4.0, 0.4

Hz, 2H, NH), 7.34-7.41 (m, 2H, ArH), 7.57 (t, J=1.8 Hz, 1H, ArH), 7.61 (t, J=1.6 Hz, 1H, ArH), 8.71 (s, 1H, NH), 10.10 (s, 1H, NH);

$^{13}$C NMR (50 MHz, acetone-$d_6$) δ21.4, 102.9, 117.7, 119.4, 120.0, 122.3, 126.2, 128.1, 130.2, 131.0, 132.4, 137.7, 144.3;

MS (EI) m/z 286 (M$^+$, 56%), 131 (M−155, 100%), 104 (M−182, 38%).

Embodiment 3

Preparation of Compound 5c
(N-(1H-Indol-7-yl)-4-methoxybenzenesulfonamide)

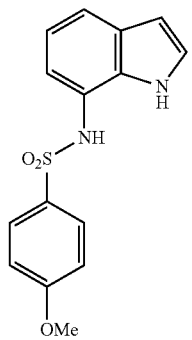

The compound 4 of the Embodiment 1 (2.00 g, 12.33 mmol) was dissolved in isopropanol (25 mL), and then Fe powder (2.07 g, 37.00 mmol) and an NH$_4$Cl solution formulated with NH$_4$Cl (0.13 g, 2.47 mmol) and water (7 mL) were added. After the resulting solution was heated at 60° C. for 2 hr, a TLC test was used to confirm the completion of the reaction. Then, active charcoal was added into the reaction solution, and stirred for 3 min. The solution was filtered, and ethyl acetate was used to wash the residue until the volume of the filtrate was 150 mL. A solution formulated with 4-methoxybenzenesulfonyl chloride (3.56 g, 17.23 mmol) and pyridine (4.00 mL, 49.70 mmol) was added into the solution. The resulting solution was stirred at room temperature for 3 hr, and a TLC test was used to confirm the completion of the reaction. After the reaction was completed, ethyl acetate was added to dilute the reaction solution to 250 mL. Then, the reaction solution was sequentially washed with 1 N of HCl, water, saturated NaHCO$_3$ solution, and brine. The color of the organic layer was red oxide after the washing steps. Na$_2$SO$_4$ was added for dehydration, and the organic layer was filtered and concentrated to obtain a solid. The solid was re-crystallized in ethanol to obtain a plate-shaped yellow solid, compound 5c (1.54 g, 30%).

mp 161-162° C. (lit.[62] 161-162° C.);

$^1$H NMR (200 MHz, CDCl$_3$) δ3.7 (s, 3H, CH$_3$), 6.43-6.46 (m, 2H, ArH), 6.72 (s, 1H, ArH), 6.76 (s, 1H, ArH), 6.78 (t, J=7.6 Hz, 1H, ArH), 7.05 (s, 1H, NH), 7.16 (t, J=2.6 Hz, 1H, ArH), 7.39 (d, J=7.4 Hz, 1H, ArH), 7.52 (s, 1H ArH), 7.56 (s, 1H ArH), 9.23 (s, 1H, NH);

$^{13}$C NMR (50 MHz, CDCl$_3$) δ56.0, 103.0, 114.6, 118.1, 120.1, 120.5, 125.5, 125.7, 129.8, 123.0, 130.4, 132.1, 163.6;

MS (EI) m/z 302 (M$^+$, 59%), 131 (M−171, 100%), 104 (M−182, 51%).

Embodiment 4

Preparation of Compound 5d
(4-Chloro-N-(1H-indol-7-yl)benzenesulfonamide)

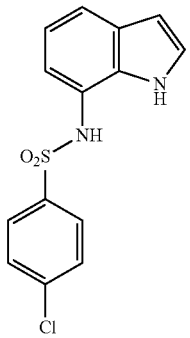

The compound 4 of the Embodiment 1 (2.48 g, 15.30 mmol) was dissolved in isopropanol (45 mL), and then Fe powder (2.56 g, 45.8 mmol) and an NH$_4$Cl solution formulated with NH$_4$Cl (0.16 g, 9 mmol) and water (9 mL) were added. After the resulting solution was heated at 60° C. for 2 hr, a TLC test was used to confirm the completion of the reaction. Then, active charcoal was added into the reaction solution, and stirred for 3 min. The solution was filtered, and ethyl acetate was used to wash the residue until the volume of the filtrate was 150 mL. A solution formulated with 4-chlorobenzenesulfonyl chloride (3.38 g, 16.00 mmol) and pyridine (3.70 mL, 45.97 mmol) was added into the solution. The resulting solution was stirred at room temperature for 7.5 hr, and a TLC test was used to confirm the completion of the reaction. After the reaction was completed, ethyl acetate was added to dilute the reaction solution to 250 mL. Then, the reaction solution was sequentially washed with 1 N of HCl, water, saturated NaHCO$_3$ solution, and brine. The color of the organic layer was red oxide after the washing steps. Na$_2$SO$_4$ was added for dehydration, and the organic layer was filtered and concentrated to obtain a solid. The solid was re-crystallized in ethanol to obtain a plate-shaped yellow solid, compound 5d (3.13 g, 67%).

mp 163-164° C. (lit. 163-164.5° C.);

$^1$H NMR (200 MHz, CDCl$_3$) δ6.44 (d, J=7.4 Hz, 1H, ArH), 6.54 (dd, J=2.2, 3.0 Hz, 1H, ArH), 6.84 (t, J=7.6 Hz, 1H, ArH), 6.96 (s, 1H, NH), 7.34-7.41 (m, 2H, ArH), 7.46-7.55 (m, 2H, ArH), 7.64-7.69 (m, 2H, ArH), 9.28 (s, 1H, NH);

$^{13}$C NMR (50 MHz, CDCl$_3$) δ103.2, 118.7, 119.8, 120.2, 120.7, 125.8, 129.3, 129.7, 130.7, 132.3, 136.6, 140.2;

MS (EI) m/z 306 (M$^+$, 25%), 131 (M−171, 90%), 104 (M−182, 100%).

Embodiment 5

Preparation of Compound 5e
(N-(1H-Indol-7-yl)-4-nitrobenzenesulfonamide)

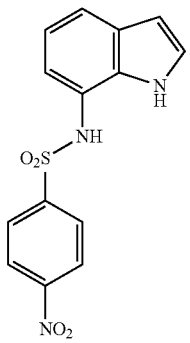

The compound 4 of the Embodiment 1 (1.36 g, 8.39 mmol) was dissolved in isopropanol (25 mL), and then Fe powder (1.40 g, 25.16 mmol) and an NH$_4$Cl solution formulated with NH$_4$Cl (0.09 g, 1.68 mmol) and water (5 mL) were added. After the resulting solution was heated at 60° C. for 1.5 hr, a TLC test was used to confirm the completion of the reaction. Then, active charcoal was added into the reaction solution, and stirred for 3 min. The solution was filtered, and ethyl acetate was used to wash the residue until the volume of the filtrate was 100 mL. A solution formulated with 4-nitrobenzenesulfonyl chloride (2.60 g, 11.74 mmol) and pyridine (3.00 mL, 33.55 mmol) was added into the solution. The resulting solution was stirred at room temperature for 3 hr, and ethyl acetate was added to dilute the reaction solution to 200 mL. Then, the reaction solution was sequentially washed with 1 N of HCl, water, saturated NaHCO$_3$ solution, and brine. The color of the organic layer was red oxide after the washing steps. Na$_2$SO$_4$ was added for dehydration, and the organic layer was filtered and concentrated to obtain a solid. The solid was re-crystallized in ethanol to obtain a plate-shaped yellow solid, compound 5e (1.93 g, 73%).

mp 185-186° C. (lit. 188-189° C.);

$^1$H NMR (200 MHz, CDCl$_3$) δ6.54 (dd, J=3.1, 2.1 Hz, 2H, ArH), 6.64 (d, J=7.4 Hz, 1H, ArH), 6.84 (t, J=7.7 Hz, 1H, ArH), 7.26-7.28 (m, 2H, ArH, NH), 7.41-7.52 (m, 2H, ArH), 7.58-7.70 (m, 2H, ArH), 7.87 (d, J=7.9, 1.2 Hz, 1H ArH), 9.06 (s, 1H, NH);

$^{13}$C NMR (50 MHz, CDCl$_3$) δ103.3, 118.8, 119.5, 120.1, 121.1, 125.7, 125.8, 130.7, 131.9, 132.6, 133.0, 134.5; MS (EI) m/z 317 (M$^+$, 37%), 206 (M−111, 58%), 131 (M−186, 100%), 104 (M−213, 79%);

HRMS (m/z) for C$_{14}$H$_1$N$_3$O$_4$S(M$^+$): Calcd, 317.0470. Found, 317.0470.

Anal. (C$_{14}$H$_{11}$N$_3$O$_4$S): Calcd, C, 52.99; H, 3.49; N, 13.24. Found, C, 52.99; H, 3.51; N, 13.07.

Embodiment 6

Preparation of Compound 5g
(N-(1H-Indol-7-yl)-4-sulfamoylbenzenesulfonamide)

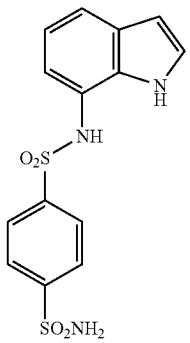

(1) Preparation of Compound 10
(4-Sulfamoylbenzenesulfonyl chloride)

Scheme II

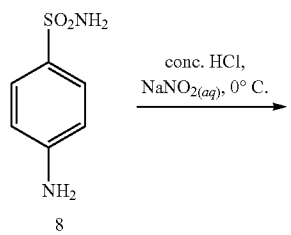

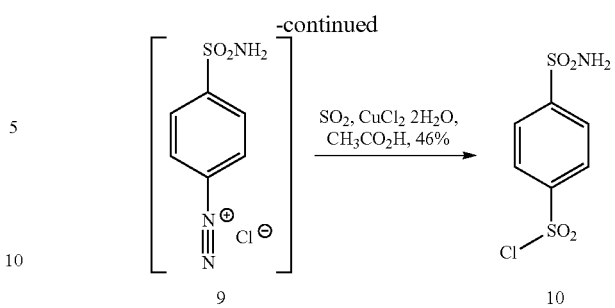

As shown in the Scheme II, a solution of the compound 9 was prepared by the following steps. First, the compound 8 (6.4 g, 37.2 mmol) was put into a flask under ice bath, water (12.5 mL) and HCl (6.30 mL, 205.68 mmol) was added, and then a solution consisting of NaNO$_2$ (2.65 g, 38.41 mmol) and water (10 mL) was added. When the solution was transformed from a state containing of white solids into a state with clear yellow color, the solution of the compound 9 was obtained. Glacial acetic acid (35 mL) was put into another flask, SO$_2$ gas was introduced into the flask for 40 min, anhydrous cupric chloride (1.5 g, 13.74 mmol) was added, and the resulting solution was stirred for 10 min. Then, the solution of the compound 9 was added dropwise. During the addition of the compound 9, white precipitates and gas were generated. After stirring for 10 min, the solution with apple green color was filtered to obtain a white solid. The white solid was washed with water, and dried to obtain a pure compound 10 (4.37 g, 46%).

mp 152-153 (lit.$^{74}$ 153-156° C.);

$^1$H NMR (200 MHz, CDCl$_3$) δ5.12 (s, 2H, NH2), 8.18 (d, J=0.6 Hz, 4H, ArH);

$^{13}$C NMR (50 MHz, CDCl$_3$) δ128.2, 144.9;

MS (EI) m/z 220 (M$^+$, 100%), 156 (M−64, 60%), 76 (M−144, 57%).

(2) Preparation of Compound 5g (N-(1H-Indol-7-yl)-4-sulfamoyl-benzenesulfonamide)

The compound 4 of the Embodiment 1 (2.00 g, 12.33 mmol) was dissolved in isopropanol (25 mL), and then Fe powder (2.07 g, 37.20 mmol) and an NH$_4$Cl solution formulated with NH$_4$Cl (0.13 g, 2.43 mmol) and water (9 mL) were added. After the resulting solution was heated at 60° C. for 1.5 hr, a TLC test was used to confirm the completion of the reaction. Then, active charcoal was added into the reaction solution, and stirred for 3 min. The solution was filtered, and ethyl acetate was used to wash the residue until the volume of the filtrate was 150 mL. The compound 10 (3.31 g, 13.3 mmol) and pyridine (3.00 mL, 33.55 mmol) was serially added into the solution. The resulting solution was stirred at room temperature for 10 hr. When the result of TLC test showed that the reaction was completed, ethyl acetate was added to dilute the reaction solution to 250 mL. Then, the reaction solution was sequentially washed with 1 N of HCl, water, saturated NaHCO$_3$ solution, and brine. The color of the organic layer was red oxide after the washing steps. Na$_2$SO$_4$ was added for dehydration, and the organic layer was filtered and concentrated to obtain a solid. The solid was re-crystallized in ethanol to obtain a needle-shaped white solid, compound 5g (2.13 g, 66%).

mp 215-216° C.;

$^1$H NMR (200 MHz, acetone-d$_6$) δ6.45 (d, J=4.2 Hz, 1H, ArH), 6.69 (d, J=7.2 Hz, 1H, ArH), 6.79 (s, 1H, NH), 6.83 (t, J=7.6 Hz, 1H, ArH), 7.34 (t, J=2.6 Hz, 1H, ArH), 7.42 (d, J=7.8 Hz, 1H, ArH), 7.85 (d, J=8.4 Hz, 2H, ArH), 7.95 (d, J=8.8 Hz, 2H, ArH), 7.99 (s, 1H, NH), 8.98 (s, 1H, NH), 10.15 (s, 1H, NH);

$^{13}$C NMR (50 MHz, acetone-d$_6$) δ102.5, 117.7, 119.6, 121.2, 125.82, 126.0, 127.1, 128.4, 130.7, 140.2, 143.2, 148.3;

MS (EI) m/z 351 (M$^+$, 53%), 131 (M–220, 100%), 104 (M–247, 47%).

Embodiment 7

Preparation of Compound 5h
(N-(1H-Indol-7-yl)-2-nitrobenzenesulfonamide)

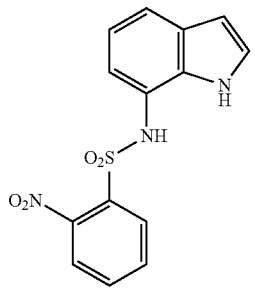

The compound 4 of the Embodiment 1 (2.00 g, 12.33 mmol) was dissolved in isopropanol (25 mL), and then Fe powder (2.07 g, 37.20 mmol) and an NH$_4$Cl solution formulated with NH$_4$Cl (0.13 g, 2.43 mmol) and water (9 mL) were added. After the resulting solution was heated at 60° C. for 1.5 hr, a TLC test was used to confirm the completion of the reaction. Then, active charcoal was added into the reaction solution, and stirred for 3 min. The solution was filtered, and ethyl acetate was used to wash the residue until the volume of the filtrate was 150 mL. 2-nitrobenzenesulfonyl chloride (3.83 g, 17.26 mmol) and pyridine (4.00 mL, 44.70 mmol) was added into the solution, and the color of the solution was transferred from light brown into dark purple. The resulting solution was stirred at room temperature for 10 hr. When the result of TLC test showed that the reaction was completed, ethyl acetate was added to dilute the reaction solution to 250 mL. Then, the reaction solution was sequentially washed with 1 N of HCl, water, saturated NaHCO$_3$ solution, and brine. The color of the organic layer was black brown, after the washing steps. Na$_2$SO$_4$ was added for dehydration, and the organic layer was filtered and concentrated to obtain a solid. The solid was re-crystallized in ethanol to obtain a plate-shaped yellow solid, compound 5h (1.61 g, 41%).

mp 187-188° C.;

$^1$H NMR (200 MHz, CDCl$_3$) δ6.55 (dd, J=0.8, 2.2 Hz, 1H, ArH), 6.62 (d, J=7.4 Hz, 1H, ArH), 6.84 (t, J=7.8 Hz, 1H, ArH), 7.26 (s, 1H, NH), 7.27 (t, J=3.0 Hz, 1H, ArH), 7.41-7.53 (m, 2H, ArH), 7.58-7.71 (m, 2H, ArH), 7.87 (dd, J=7.0, 0.8 Hz, 1H, ArH), 9.04 (s, 1H, NH);

$^{13}$C NMR (50 MHz, CDCl$_3$) δ103.3, 118.8, 119.4, 120.1, 121.1, 125.7, 125.8, 130.7, 131.9, 132.6, 132.9, 134.5;

MS (EI) m/z 317 (M$^+$, 35%), 131 (M–186, 88%), 104 (M–213, 100%), 77 (M–240, 26%);

HRMS (m/z) for C$_{14}$H$_{11}$N$_3$O$_4$S(M$^+$): Calcd, 317.0470. Found, 317.0476.

Anal. (C$_{14}$H$_{11}$N$_3$O$_4$S): Calcd, C, 52.99; H, 3.49; N, 13.24. Found, C, 52.69; H, 3.59; N, 13.13.

Embodiment 8

Preparation of Compound 6a (N-(5,8-Dimethyl-9H-carbazol-1-yl)benzenesulfonamide)

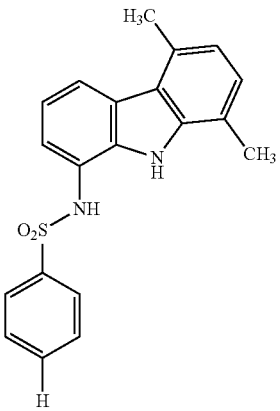

The compound 5a (0.85 g, 3.12 mmol) and ethanol (25 mL) were added into a three-necked flask, and mixed well. Then, p-toluene sulfonic acid (0.30 g, 1.56 mmol) and hexane-2,5-dione (0.71 g, 6.24 mmol) were added. The resulting solution was heated at reflux for 4.5 hr, and a TLC test was used to check the condition of the reaction. When the result of the TLC test showed that the amount of the starting materials stopped decreasing, the purple ethanol solution was evaporated. Then, ethyl acetate was added, and the residue was extracted with water. Na$_2$SO$_4$ was added into the organic layer to remove water, the organic layer was filtered, and ethyl acetate in the filtrate was evaporated to obtain a solid. The solid was purified with column chromatography (silica gel: φ4 cm×16 cm; eluent: hexane/ethyl acetate=7/5). The liquid was collected (R$_f$=0.61, hexane/ethyl acetate=7/5), and concentrated to obtain a white solid, compound 6a (0.47 g, 43%).

mp 237-238° C.;

$^1$H NMR (200 MHz, acetone-d$_6$) δ2.52 (s, 3H, CH$_3$), 2.76 (s, 3H, CH$_3$), 6.89 (d, J=3.6 Hz, 1H, ArH), 7.01-7.08 (m, 3H, ArH), 7.38-7.54 (m, 3H, ArH), 7.73-7.78 (m, 2H, ArH), 7.98 (d, J=3.8 Hz, 1H, ArH), 8.82 (s, 1H, NH), 9.83 (s, 1H, NH);

$^{13}$C NMR (50 MHz, CDCl$_3$) δ17.0, 20.8, 118.3, 118.8, 119.4, 119.8, 121.6, 122.3, 122.6, 127.2, 127.3, 127.9, 129.3, 129.7, 131.2, 136.6, 139.6, 140.3.

Embodiment 9

Preparation of Compound 6b (N-(5,8-Dimethyl-9H-carbazol-1-yl)-4-methylbenzenesulfonamide)

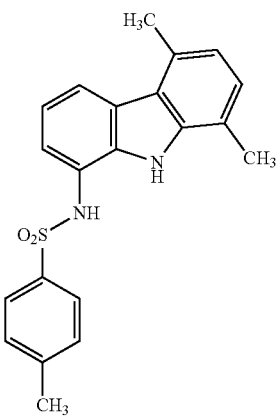

The compound 5b (1.00 g, 3.49 mmol) and ethanol (25 mL) were added into a three-necked flask, and mixed well. Then, p-toluene sulfonic acid (0.33 g, 1.75 mmol) and hexane-2,5-dione (0.80 g, 6.98 mmol) were added. The resulting solution was heated at reflux for 36 hr, and a TLC test was used to check the condition of the reaction. When the result of the TLC test showed that the reaction was completed, the ethanol solution was evaporated. Then, ethyl acetate was added and the residue was extracted with water. Na$_2$SO$_4$ was added into the organic layer to remove water, the organic layer was filtered, and ethyl acetate in the filtrate was evaporated to obtain a solid. The solid was purified with column chromatography (silica gel: φ4 cm×13 cm; eluent: hexane/ethyl acetate=7/5). The liquid was collected (R$_f$=0.57, hexane/ethyl acetate=7/5), and concentrated to obtain a white solid, compound 6b (1.26 g, 99%).

mp 185-186° C.;

$^1$H NMR (400 MHz, CDCl$_3$) δ2.33 (s, 3H, CH$_3$), 2.52 (s, 3H, CH$_3$), 2.79 (s, 3H, CH$_3$), 6.71 (d, J=3.8 Hz, 1H, ArH), 6.92 (d, J=3.6 Hz, 1H, ArH), 6.97 (t, J=3.9 Hz, 1H, ArH), 7.01 (s, 1H, NH), 7.15 (t, J=4.1 Hz, 3H, ArH), 7.59 (d, J=4.1 Hz, 2H, ArH), 7.98 (d, J=7.8 Hz, 1H, ArH), 9.07 (s, 1H, NH);

$^{13}$C NMR (100 MHz, CDCl$_3$) δ16.5, 20.4, 21.5, 117.9, 119.1, 119.214, 121.113, 121.2, 121.3, 121.5, 126.6, 126.6, 127.5, 129.7, 130.7, 134.9, 135.7, 139.1, 144.2;

MS (EI) m/z 364 (M$^+$, 23%), 209 (M−155, 100%), 28 (M−336, 37%);

HRMS (m/z) for C$_{21}$H$^{20}$N$_2$O$_2$S(M$^+$): Calcd, 364.1245. Found, 364.1247.

Anal. (C$_{21}$H$_{20}$N$_2$O$_2$S): Calcd, C, 69.20; H, 5.53; N, 7.69. Found, C, 69.23; H, 5.53; N, 7.56.

Embodiment 10

Preparation of Compound 6c (N-(5,8-Dimethyl-9H-carbazol-1-yl)-4-methoxybenzenesulfonamide)

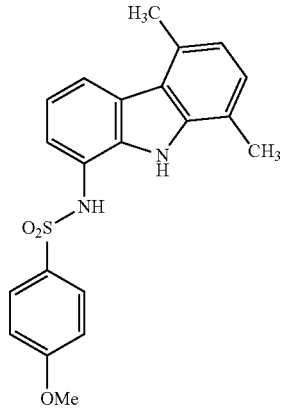

The compound 5c (0.70 g, 2.32 mmol) and ethanol (25 mL) were added into a three-necked flask, and mixed well. Then, p-toluene sulfonic acid (0.22 g, 1.16 mmol) and hexane-2,5-dione (0.53 g, 4.63 mmol) were added. The resulting solution was heated at reflux for 6 hr, and a TLC test was used to check the condition of the reaction. When the result of the TLC test showed that the amount of the starting materials stopped decreasing, the ethanol solution was evaporated. Then, ethyl acetate was added and the residue was extracted with water. Na$_2$SO$_4$ was added into the organic layer to remove water, the organic layer was filtered, and ethyl acetate in the filtrate was evaporated to obtain a solid. The solid was purified with column chromatography (silica gel: φ4 cm×11 cm; eluent: hexane/ethyl acetate=7/5). The liquid was collected (R$_f$=0.56, hexane/ethyl acetate=7/5), and concentrated to obtain a white solid, compound 6c (0.20 g, 23%).

mp 180.5-181° C.;

$^1$H NMR (200 MHz, CDCl$_3$) δ2.54 (s, 3H, CH$_3$), 2.80 (s, 3H, CH$_3$), 3.77 (s, 3H, OCH$_3$), 6.69 (d, 1=7.6 Hz, 1H, ArH), 6.79 (s, 1H, ArH), 6.84 (s, 1H, ArH), 6.90 (s, 1H, NH), 6.96 (dd, J=7.6, 7.8 Hz, 2H, ArH), 7.14 (d, J=7.4 Hz, 1H, ArH), 7.60 (t, J=2.0 Hz, 1H, ArH), 7.63 (t, J=2.0 Hz, 1H, ArH), 7.99 (d, 1=8.0 Hz, 1H, ArH), 9.09 (s, 1H, NH);

$^{13}$C NMR (50 MHz, CDCl$_3$) δ21.0, 24.8, 60.2, 119.0, 122.7, 124.2, 125.0, 125.1, 125.9, 126.1, 130.8, 131.4, 134.4, 135.3, 136.4, 139.5, 144.1, 168.1;

MS (EI) m/z 380 (M$^+$, 55%), 209 (M−171, 100%). Anal. (C$_{21}$H$_{20}$N$_2$O$_3$S): Calcd, C, 66.29; H, 5.30; N, 7.36. Found, C, 66.05; H, 5.37; N, 7.06.

Embodiment 11

Preparation of Compound 6d (4-Chloro-N-(5,8-dimethyl-9H-carbazol-1-yl)benzenesulfonamide)

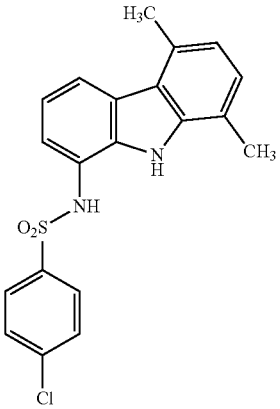

The compound 5d (1.00 g, 3.26 mmol) and ethanol (25 mL) were added into a three-necked flask, and mixed well. Then, p-toluene sulfonic acid (0.30 g, 1.60 mmol) and hexane-2,5-dione (0.74 g, 6.52 mmol) were added. The resulting solution was heated at reflux for 9 hr, and a TLC test was used to check the condition of the reaction. When the result of the TLC test showed that the amount of the starting materials stopped decreasing, the ethanol solution was evaporated. Then, ethyl acetate was added and the residue was extracted with water. Na$_2$SO$_4$ was added into the organic layer to remove water, the organic layer was filtered, and ethyl acetate in the filtrate was evaporated to obtain a solid. The solid was purified with column chromatography (silica gel: φ4 cm×15 cm; eluent: hexane/ethyl acetate=7/5). The liquid was collected (R$_f$=0.57, hexane/ethyl acetate=7/5), and concentrated to obtain a white solid, compound 6d (0.67 g, 53.25%).

mp 217-218° C.;

$^1$H NMR (200 MHz, acetone-d$_6$) δ2.52 (s, 3H, CH$_3$), 2.77 (s, 3H, CH$_3$), 6.90 (d, J=7.2 Hz, 1H, ArH), 7.05-7.17 (m, 3H, ArH), 7.46-7.53 (m, 2H, ArH), 7.72 (t, J=2.1 Hz, 1H, ArH), 7.75 (m, 1H, ArH), 7.89 (dd, J=7.3, 1.6 Hz, 1H, ArH), 8.88 (s, 1H, NH), 9.84 (s, 1H, NH);

$^{13}$C NMR (50 MHz, acetone-d$_6$) δ16.8, 20.5, 118.5, 120.0, 121.2, 121.5, 121.8, 122.0, 126.7, 127.3, 128.1, 129.8, 131.2, 133.7, 135.6, 139.9, 140.6;

MS (EI) m/z 384 (M+, 27%), 209 (M−175, 100%), 28 (M−356, 60%);

HRMS (m/z) for $C_{20}H_{17}ClN_2O_2S(M^+)$: Calcd, 384.0699. Found, 384.0700.

Anal. ($C_{20}H_{17}ClN_2O_2S$): Calcd, C, 62.41; H, 4.45; N, 7.28. Found, C, 62.42; H, 4.48; N, 7.14.

Embodiment 12

Preparation of Compound 6e (N-(5,8-Dimethyl-9H-carbazol-1-yl)-4-nitrobenzenesulfonamide)

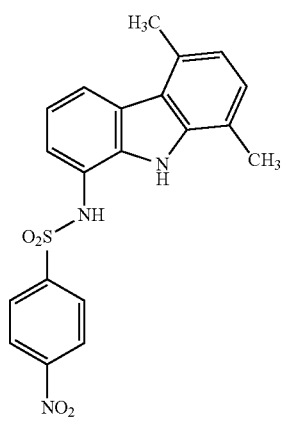

The compound 5e (1.00 g, 3.15 mmol) and ethanol (25 mL) were added into a three-necked flask, and mixed well. Then, p-toluene sulfonic acid (0.30 g, 1.58 mmol) and hexane-2,5-dione (0.72 g, 6.30 mmol) were added. The resulting solution was heated at reflux for 5 hr, and a TLC test was used to check the condition of the reaction. When the result of the TLC test showed that the amount of the starting materials stopped decreasing and the reaction was in a balance state, the ethanol solution was evaporated. Then, ethyl acetate was added and the residue was extracted with water. $Na_2SO_4$ was added into the organic layer to remove water, the organic layer was filtered, and ethyl acetate in the filtrate was evaporated to obtain a solid. The solid was purified with column chromatography (silica gel: φ4 cm×10 cm; eluent: hexane/ethyl acetate=3/1). The liquid was collected ($R_f$=0.34, hexane/ethyl acetate=3/1), and concentrated to obtain a white solid, compound 6e (0.31 g, 79%). Another liquid was also collected ($R_f$=0.26, hexane/ethyl acetate=3/1), and concentrated to recycle the compound 5e (0.21 g).

mp 202-203° C.;

$^1$H NMR (200 MHz, $CDCl_3$) δ2.55 (s, 3H, $CH_3$), 2.79 (s, 3H, $CH_3$), 6.89 (dd, J=7.7, 1.0 Hz, 1H, ArH), 6.92-7.03 (m, 2H, ArH), 7.16 (d, J=7.2 Hz, 1H, ArH), 7.31 (s, 1H, NH), 7.42 (ddd, J=1.2, 7.4, 7.9 Hz, 1H, ArH), 7.58 (dd, J=7.9, 1.4 Hz, 1H, ArH), 7.66 (ddd, J=1.6, 8.5, 6.9 Hz, 1H, ArH), 7.87 (dd, J=8.0, 1.2 Hz, 1H, ArH), 8.02 (dd, J=1.0, 2.8 Hz, 1H, ArH), 8.88 (s, 1H, NH);

$^{13}$C NMR (50 MHz, $CDCl_3$) δ17.0, 20.8, 118.3, 118.5, 119.8, 121.6, 121.8, 122.3, 122.9, 125.6, 127.3, 131.2, 131.9, 132.6, 132.9, 134.6, 136.7, 139.5, 148.6, 161.8;

MS (EI) m/z 396 (M+1, 38%), 395 (M+, 12%), 209 (M−186, 100%). Anal. ($C_{20}H_{17}N_3O_4S$): Calcd, C, 60.75; H, 4.33; N, 10.63. Found, C, 60.46; H, 4.29; N, 10.37.

Embodiment 13

Preparation of Compound 6f (4-Amino-N-(5,8-dimethyl-9H-carbazol-1-yl)benzenesulfonamide)

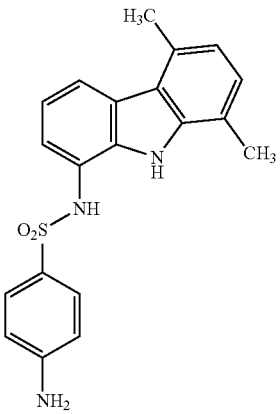

The compound 6e (0.15 g, 0.38 mmol) was dissolved in isopropanol (25 mL), and then Fe powder (64 mg, 1.14 mmol) and an $NH_4Cl$ solution formulated with $NH_4Cl$ (4.1 mg, 0.07 mmol) and water (0.5 mL) were added. The resulting solution was stirred and heated to 60° C. After heating for 1 hr, a TLC test was used to confirm the completion of the reaction. Then, active charcoal was added into the reaction solution, and stirred for 3 min. The solution was filtered, and ethyl acetate was used to wash the residue. The filtrate was dried to obtain a solid, and the solid was purified with column chromatography (silica gel: φ1.5 cm×10 cm; eluent: hexane/ethyl acetate=3/1). The liquid was collected ($R_f$=0.24, hexane/ethyl acetate=2/1), and concentrated to obtain a white solid, compound 6f (0.08 g, 58%).

mp 254-255° C.;

$^1$H NMR (200 MHz, acetone-$d_6$) δ2.51 (s, 3H, $CH_3$), 2.74 (s, 3H, $CH_3$), 3.12 (s, 2H, $NH_2$), 6.87 (d, J=7.0 Hz, 1H, ArH), 7.04-7.17 (m, 3H, ArH), 7.97-8.01 (m, 3H, ArH), 8.24-8.28 (m, 2H, ArH), 9.14 (s, 1H, NH), 9.95 (s, 1H, NH);

$^{13}$C NMR (50 MHz, acetone-$d_6$) δ17.0, 20.8, 118.2, 118.4, 119.4, 121.6, 121.9, 122.4, 122.9, 125.6, 127.3, 131.2, 131.9, 132.7, 133.0, 134.5, 136.6, 139.5, 148.6, 161.8.

Embodiment 14

Preparation of Compound 6g (N-(5,8-Dimethyl-9H-carbazol-1-yl)-4-sulfamoylbenzenesulfonamide)

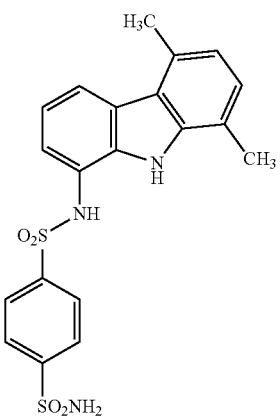

The compound 5g (1.00 g, 2.85 mmol) and ethanol (25 mL) were added into a three-necked flask, and mixed well. Then, p-toluene sulfonic acid (0.27 g, 1.43 mmol) and hexane-2,5-dione (0.65 g, 5.70 mmol) were added. The resulting solution was heated at reflux for 5 hr, and a TLC test was used to check the condition of the reaction. When the result of the TLC test showed that the reaction was completed, the ethanol solution was evaporated. Then, ethyl acetate was added and the residue was extracted with water. $Na_2SO_4$ was added into the organic layer to remove water, the organic layer was filtered, and ethyl acetate in the filtrate was evaporated to obtain a solid. The solid was purified with column chromatography (silica gel: φ4 cm×7 cm; eluent: hexane/ethyl acetate=3/1). The liquid was collected ($R_f$=0.39, hexane/ethyl acetate=2/1), and concentrated to obtain a white solid, compound 6g (1.06 g, 86%).

mp 290-291° C.;

$^1$H NMR (400 MHz, DMSO-$d_6$) δ2.50 (s, 3H, $CH_3$), 2.69 (s, 3H, $CH_3$), 6.85 (d, J=7.2 Hz, 1H, ArH), 7.05 (t, J=8.0 Hz, 1H, ArH), 7.09 (d, J=7.2 Hz, 1H, ArH), 7.24 (d, J=7.6 Hz, 1H, ArH), 7.47 (s, 2H, $NH_2$), 7.84 (d, J=7.6 Hz, 1H, ArH), 7.90 (d, J=8.0 Hz, 2H, ArH), 7.87 (d, J=8.0 Hz, 2H, ArH), 8.00 (d, J=8.4 Hz, 2H, ArH), 10.22 (s, 1H, NH), 10.63 (s, 1H, NH);

$^{13}$C NMR (100 MHz, DMSO-$d_6$) δ16.5, 20.3, 116.2, 117.4, 119.5, 120.1, 120.3, 124.8, 126.3, 126.6, 127.9, 129.1, 138.6, 147.7;

MS (EI) m/z 429 ($M^+$, 55%), 209 (M−220, 100%), 28 (M−401, 50%);

HRMS (m/z) for $C_{20}H_{19}N_3O_4S(M^+)$: Calcd, 429.0817. Found, 429.0816.

Anal. ($C_{20}H_{19}N_3O_4S$): Calcd, C, 55.93; H, 4.46; N, 9.78. Found, C, 55.77; H, 4.57; N, 9.64.

Embodiment 15

Preparation of Compound 6h (N-(5,8-Dimethyl-9H-carbazol-1-yl)-2-nitrobenzenesulfonamide)

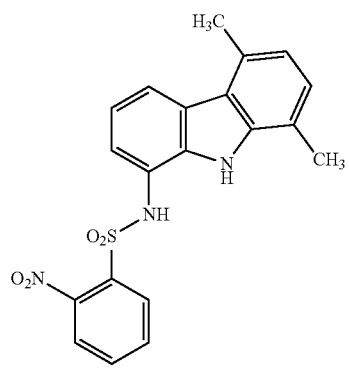

The compound 5h (0.60 g, 1.89 mmol) and ethanol (25 mL) were added into a three-necked flask, and mixed well. Then, p-toluene sulfonic acid (0.18 g, 0.95 mmol) and hexane-2,5-dione (0.43 g, 3.78 mmol) were added. The resulting solution was heated at reflux for 3 hr, and a creamy solid was formed. After the reaction was performed for 20 hr, a TLC test was used to check whether the amount of the starting materials stopped decreasing and the reaction was in a balance state. When the result of the TLC test showed that the reaction was completed, the ethanol solution was filtered and evaporated. Then, the residue was dissolved with ethyl acetate and washed with water. $Na_2SO_4$ was added into the organic layer to remove water, and the organic layer was filtered. Active charcoal was added into the filtrate, and the filtrate was heated, stirred, filtered, and evaporated to obtain a green solid. The green solid was purified with column chromatography (silica gel: φ4 c×15 cm; eluent: hexane/ethyl acetate=3/1). The liquid was collected ($R_f$=0.67, hexane/ethyl acetate=3/1), and concentrated to obtain a white solid, compound 6h (0.48 g, 65%).

mp 202-203° C.;

$^1$H NMR (200 MHz, acetone-$d_6$) δ2.53 (s, 3H, $CH_3$), 2.76 (s, 3H, $CH_3$), 6.90 (d, J=7.2 Hz, 1H, ArH), 7.05-7.14 (m, 2H, ArH), 7.23 (dd, J=1.2, 3.9 Hz, 1H, ArH), 7.31 (s, 1H, NH), 7.63 (dt, J=1.4, 7.6 Hz, 1H, ArH), 7.76-7.85 (m, 2H, ArH), 7.95 (dt, J=1.2, 8.2 Hz, 1H, ArH), 8.04 (dd, J=0.8, 7.7 Hz, 1H, ArH), 9.10 (s, 1H, NH), 9.96 (s, 1H, NH);

$^{13}$C NMR (50 MHz, acetone-$d_6$) δ16.4, 20.2, 118.2, 119.6, 119.8, 121.5, 121.7, 125.3, 126.5, 127.1, 130.8, 131.9, 132.2, 132.6, 135.0, 136.0, 140.0, 148.7;

MS (EI) m/z 395 ($M^+$, 17%), 209 (M−186, 100%);

HRMS (m/z) for $C_{20}H_{17}N_3O_4S(M^+)$: Calcd, 395.0940. Found, 395.0941.

Anal. ($C_{20}H_{17}N_3O_4S$): Calcd, C, 60.75; H, 4.33; N, 10.63. Found, C, 60.66; H, 4.41; N, 10.40.

Embodiment 16

Preparation of Compound 7a (4-Chloro-N-[3-(4-nitrophenylazo)-1H-indol-7-yl]benzenesulfonamide)

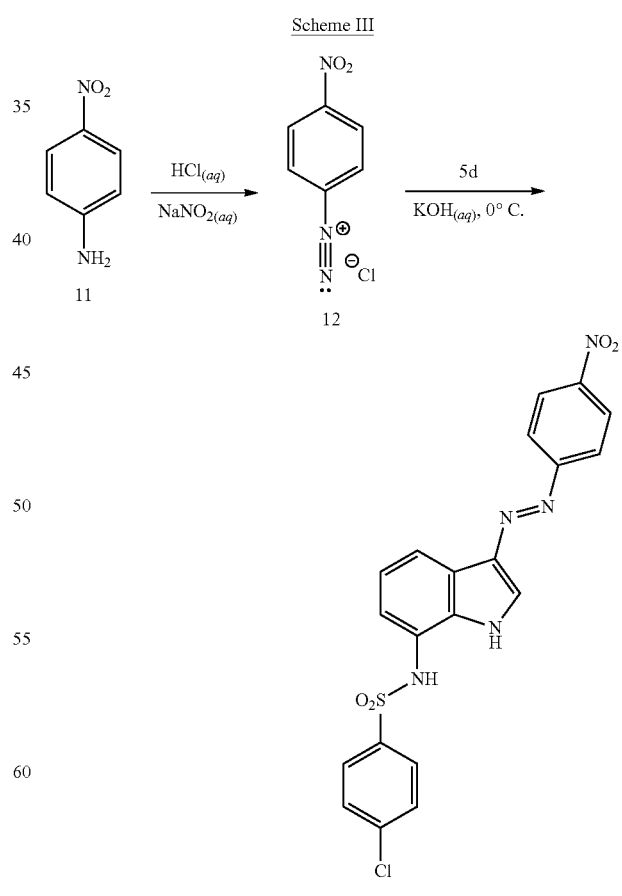

As shown in the Scheme III, a solution of the compound 12 was prepared by the following steps. First, the compound 11 (4-nitroaniline, 1.15 g, 8.29 mmol) was put into a flask under ice bath, HCl (9.29 mL) was added, and then water was added to dilute the solution to 100 mL. A solution consisting of NaNO$_2$ (0.95 g, 13.80 mmol) and water (25 mL) was added dropwise. When the state of the solution was turned into yellow and clear, the solution of the compound 12 was obtained. In another flask under ice bath, the compound 5d (2 g, 6.52 mmol) was added into cold water (20 g), and the resulting solution was stirred. Then, a KOH solution formulated with KOH (1.90 g, 33.90 mmol) and water (280 mL) was added, the resulting solution was stirred until all the solids were dissolved and the solution was in a clear state. Next, the solution of the compound 12 was added. During the addition of the solution of the compound 12, precipitates with dark red color were formed. After stirring the resulting solution for 10 min, the resulting solution was filtered, and the dark red solid was dried. The dark red solid was purified with column chromatography (silica gel: ϕ4 cm×18 cm; eluent: hexane/ethyl acetate=7/5). The liquid was collected (R$_f$=0.48, hexane/ethyl acetate=7/5), and concentrated to obtain a dark red solid, compound 7a (0.63 g, 21%).

mp 217-218° C.;

$^1$H NMR (200 MHz, CDCl$_3$) δ6.78 (d, J=7.9 Hz, 1H, ArH), 7.24-7.38 (m, 4H, ArH), 7.57-7.70 (m, 3H, ArH), 8.00 (d, J=8.0 Hz, 2H, ArH), 8.33 (d, J=8.1 Hz, 2H, ArH), 9.81 (s, 1H, NH);

$^{13}$C NMR (50 MHz, acetone-d$_6$) δ104.1, 115.5, 122.0, 123.3, 124.9, 125.2, 126.4, 129.4, 129.7, 129.8, 131.7, 138.6, 139.3, 143.2, 148.7, 157.1;

MS (EI) m/z 455 (M$^+$, 44%), 280 (M−175, 85%), 234 (M−221, 66%), 130 (M−325, 52%);

HRMS (m/z) for C$_{20}$H$_{14}$ClN$_5$O$_4$S(M$^+$): Calcd, 455.0455. Found, 455.0424.

Anal. (C$_{20}$H$_{14}$ClN$_5$O$_4$S): Calcd, C, 52.69; H, 3.10; N, 15.36. Found, C, 52.44; H, 3.17; N, 15.08.

Embodiment 17

Preparation of Compound 7b (4-Methyl-N-(3-phenylazo-1H-indol-7-yl)benzenesulfonamide)

Scheme IV

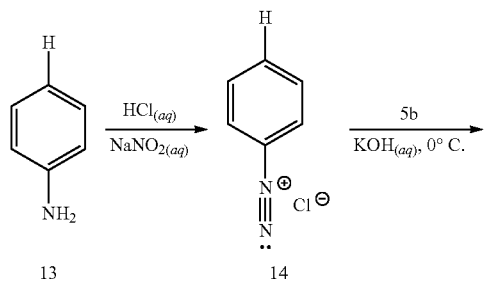

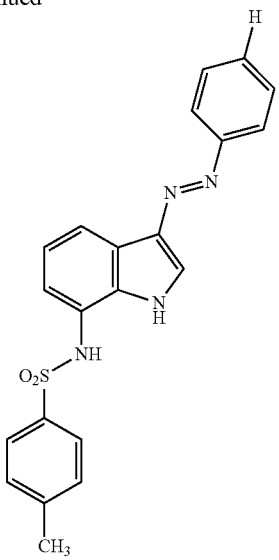

7b

As shown in the Scheme IV, a solution of the compound 14 was prepared by the following steps. First, the compound 13 (aniline, 0.15 g, 1.63 mmol) was put into a flask under ice bath, HCl (1.83 mL) was added, and then water was added to dilute the solution to 20 mL. A solution consisting of NaNO$_2$ (0.19 g, 2.72 mmol) and water (5 mL) was added dropwise. When the state of the solution was turned into yellow and clear, the solution of the compound 14 was obtained. In another flask under ice bath, the compound 5b (0.36 g, 1.26 mmol) was added into cold water (5 g), and the resulting solution was stirred. Then, a KOH solution formulated with KOH (0.36 g, 6.42 mmol) and water (54 mL) was added, the resulting solution was stirred until all the solids were dissolved and the solution was in a clear state. Next, the solution of the compound 14 was added. During the addition of the solution of the compound 14, precipitates with dark red color were formed. After stirring the resulting solution for 10 min, the resulting solution was filtered, and the dark red solid was dried. The dark red solid was purified with column chromatography (silica gel: ϕ4 cm×13 cm; eluent: hexane/ethyl acetate=3/1). The liquid was collected (R$_f$=0.39, hexane/ethyl acetate=3/1), and concentrated to obtain a dark red solid, compound 7b (0.04 g, 0.14 mmol).

mp 212-213° C.;

$^1$NMR (200 MHz, CDCl$_3$) δ2.30 (s, 3H, CH$_3$), 6.82 (d, J=8.0 Hz, 1H, ArH), 7.14 (d, J=8.0 Hz, 2H, ArH), 7.40-7.34 (m, 2H, ArH), 7.42-7.55 (m, 3H, ArH), 7.60 (d, J=8.0 Hz, 1H, ArH), 7.64 (s, 1H, ArH), 7.68 (s, 1H, ArH), 7.83 (s, 1H, NH), 7.93 (t, J=1.4 Hz, 1H, ArH), 7.96 (t, J=1.8 Hz, 1H, ArH), 9.65 (s, 1H, NH);

$^{13}$C NMR (50 MHz, CDCl$_3$) δ22.0, 104.0, 116.9, 121.2, 122.8, 123.0, 123.5, 127.8, 128.8, 129.48, 130.3, 130.9, 132.4, 135.2, 143.8, 145.0, 153.8;

MS (EI) m/z 390 (M$^+$, 58%), 235 (M−155, 100%), 28 (M−362, 86%).

Embodiment 18

Preparation of Compound 7c (4-Chloro-N-(3-phenylazo-1H-indol-7-yl)benzenesulfonamide)

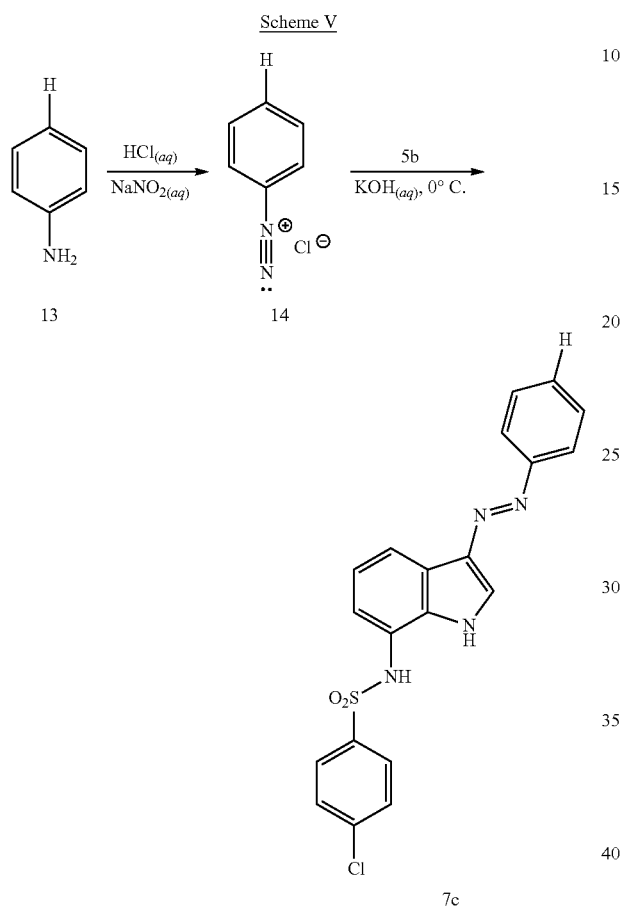

As shown in the Scheme V, a solution of the compound 14 was prepared by the following steps. First, the compound 13 (0.18 g, 1.91 mmol) was put into a flask under ice bath, HCl (2.14 mL) was added, a solution consisting of NaNO$_2$ (0.21 g, 3.05 mmol) and water (5 mL) was added dropwise, and then water was added to dilute the solution to 20 mL. When the state of the solution was turned into yellow and clear, the solution of the compound 14 was obtained. In another flask under ice bath, the compound 5d (0.45 g, 1.26 mmol) was added into cold water (5 g), and the resulting solution was stirred. Then, a KOH solution formulated with KOH (0.42 g, 7.49 mmol) and water (63 mL) was added, the resulting solution was stirred until all the solids were dissolved and the solution was in a clear state. Next, the solution of the compound 14 was added. During the addition of the solution of the compound 14, precipitates with red oxide color were formed. After stirring the resulting solution for 10 min, the resulting solution was filtered, and the red oxide solid was dried. The red oxide solid was purified with column chromatography (silica gel: φ4 cm×21 cm; eluent: hexane/ethyl acetate=3/1). The liquid was collected ($R_f$=0.40, hexane/ethyl acetate=3/1), and concentrated to obtain the compound 7c (0.23 g, 54%). In addition, another liquid also was collected ($R_f$=0.31, hexane/ethyl acetate=3/1), and concentrated to obtain a red oxide solid, compound 5d (0.13 g, 0.42 mmol).

mp 110-111° C.;
$^1$H NMR (200 MHz, CDCl$_3$) δ 6.70 (d, J=8.0 Hz, 1H, ArH), 7.34 (d, J=8.6 Hz, 3H, ArH), 7.34-7.50 (m, 5H, ArH, NH), 7.62 (d, J=8.2 Hz, 3H, ArH), 7.94 (d, J=8.6 Hz, 2H, ArH), 9.42 (s, 1H, NH);
$^{13}$C NMR (50 MHz, CDCl$_3$) δ 103.2, 119.5, 120.8, 121.0, 121.3, 121.5, 126.3, 126.8, 127.6, 129.3, 130.7, 133.2, 139.4, 140.1, 145.1, 154.7;
MS (EI) m/z 410 (M$^+$, 33%), 235 (M-175, 100%), 130 (M-280, 48%), 111 (M-299, 55%);
HRMS (m/z) for C$_{20}$H$_{15}$ClN$_4$O$_2$S(M$^+$): Calcd, 410.0604. Found, 410.0607.

Embodiment 19

Preparation of Compound 6i (N-(5,8-Dimethyl-9H-carbazol-1-yl)-3,4,5-trimethoxybenzenesulfonamide))

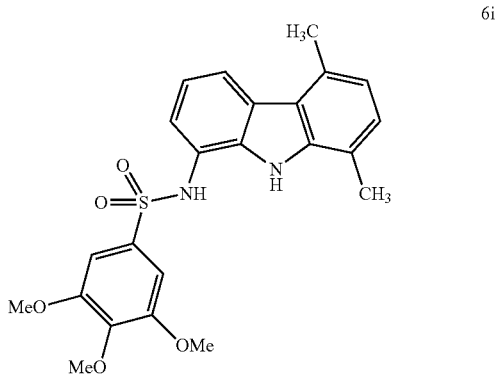

A mixture of 4 (0.5 g, 3.08 mmol) and 10% Pd/C (0.2 g) in methanol (30 mL) was stirred under hydrogen for 1 hour. Pd/C was removed by filtration and filtrate was evaporated in vacuo to yield oily product. To the product, ethyl acetate (30 mL) and 3,4,5-trimethoxybenzenesulfonyl chloride (0.9 g, 3.38 mmol) were added and stirred at 50° C. for 1 hour. The reaction was roughly purified by passing through silica gel packed funnel and wash with ethyl acetate. The filtrate was evaporated in vacuo and the crude product was reacted with acetonylacetone (0.5 mL, 4.38 mmol) in the presence of p-toluenesulfonic acid (0.7 g, 4.06 mmol) in EtOH (20 mL) at reflux for 3 hours. Finally, the mixture was purified with column chromatography and recrystallization in ethanol to afford white solids, compound 6i (0.66 g, 48.37%; Hex/EA=4/1, $R_f$=0.2).

mp=205-207° C.;
ESI (M-H$^+$) 439.1;
$^1$H NMR (200 Hz, DMSO-d$_6$) δ 2.07 (s, 3H, CH$_3$), 2.68 (s, 3H, CH$_3$), 3.43 (s, 3H, OCH$_3$), 3.62 (s, 6H, OCH$_3$), 6.82 (d, J=7.2 Hz, 1H, ArH), 6.95 (s, 2H, ArH), 7.00-7.15 (m, 2H, ArH), 7.37 (d, J=7.6 Hz, 1H, ArH), 7.87 (d, J=7.6 Hz, 1H, ArH), 7.72 (s, 1H, NH), 10.51 (s, 1H, NH);
$^{13}$C NMR (50 Hz, DMSO-d$_6$) δ 16.37, 20.07, 55.99, 59.87, 104.24, 117.27, 118.38, 119.12, 119.31, 120.32, 120.56, 121.15, 124.77, 126.15, 129.82, 132.85, 133.96, 138.45, 140.67, 152.50.
Anal. (C$_{23}$H$_{24}$N$_2$O$_5$S): Calcd, C, 62.71; H, 5.49; N, 6.36; S, 7.28. Found, C, 62.75; H, 5.69; N, 6.59; S, 7.10.

Embodiment 20

Preparation of Compound 6j (N-(5,8-Dimethyl-9H-carbazol-1-yl)-3-trifluoromethylbenzenesulfonamide))

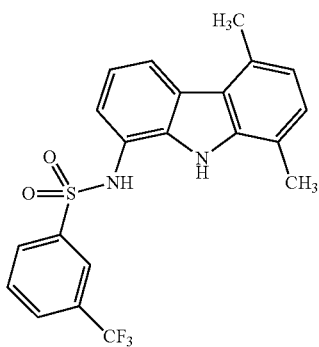

6j

A mixture of 4 (0.5 g, 3.08 mmol) and 10% Pd/C (0.2 g) in methanol (30 mL) was stirred under hydrogen for 1 hour. Pd/C was removed by filtration and filtrate was evaporated in vacuo to yield oily product. To the product, ethyl acetate (30 mL) and 3-trifluoromethylbenzenesulfonyl chloride (0.8 g, 3.27 mmol) were added and stirred at 50° C. for 1 hour. The reaction was roughly purified by passing through silica gel packed funnel and wash with ethyl acetate. The filtrate was evaporated in vacuo and the crude product was reacted with acetonylacetone (0.5 mL, 4.38 mmol) in the presence of p-toluenesulfonic acid (0.7 g, 4.06 mmol) in EtOH (20 mL) at reflux for 3 hours. Finally, the mixture was purified with column chromatography to afford white solids, compound 6j (2.01 g, 78.08%; Hex/EA=8/1, $R_f$=0.15).

mp=217-218° C.;

ESI (M-H$^+$) 417.1;

$^1$H NMR (400 Hz, DMSO-d$_6$) δ 2.43 (s, 3H, CH$_3$), 2.66 (s, 3H, CH$_3$), 6.82 (d, J=7.2 Hz, 1H, ArH), 7.05-7.11 (m, 2H, ArH), 7.27 (d, J=7.6 Hz, 1H, ArH), 7.62 (t, J=8.0 Hz, 1H, ArH), 7.86 (t, J=7.6 Hz, 2H, ArH), 7.92 (d, J=8.0 Hz, 1H, ArH), 8.13 (s, 1H, ArH), 9.97 (s, 1H, ArH), 10.50 (s, 1H, NH);

$^{13}$C NMR (100 Hz, DMSO-d$_6$) δ 16.28, 19.98, 111.40, 118.71, 119.07, 119.73, 120.18, 120.32, 120.60, 121.88, 123.39, 123.43, 123.47, 124.59, 124.96, 126.20, 129.49, 129.60, 129.64, 129.77, 129.82, 130.56, 130.80, 132.99, 138.56, 140.52.

Anal. (C$_{21}$N$_{17}$F$_3$N$_2$O$_2$S): Calcd, C, 60.28; H, 4.10; N, 6.69; F, 13.62; S, 7.66. Found, C, 75.89; H, 5.88; N, 12.76.

Embodiment 21

Preparation of Compound 6k (5-Chloro-thiophene-2-sulfonic acid (5,8-dimethyl-9H-carbazol-1-yl)amide))

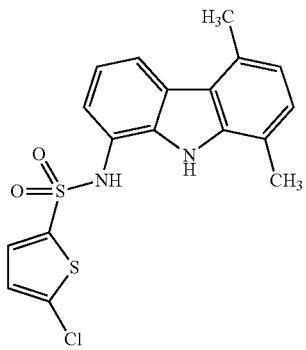

6k

A mixture of 4 (0.5 g, 3.08 mmol) and 10% Pd/C (0.2 g) in methanol (30 mL) was stirred under hydrogen for 1 hour. Pd/C was removed by filtration and filtrate was evaporated in vacuo to yield oily product. To the product, ethyl acetate (30 mL) and 5-chloro-thiophene-2-sulfonyl chloride (0.7 g, 3.24 mmol) were added and stirred at room temperature for 1 hour. The reaction was roughly purified by passing through silica gel packed funnel and wash with ethyl acetate. The filtrate was evaporated in vacuo and the crude product was reacted with acetonylacetone (0.5 mL, 4.38 mmol) in the presence of p-toluenesulfonic acid (0.7 g, 4.06 mmol) in EtOH (20 mL) at reflux for 3 hours. Finally, the mixture was purified with column chromatography to afford white solids, compound 6k (0.87 g, 72.40%; Hex/EA=8/1, $R_f$=0.33).

mp=232-234° C.;

ESI (M-H$^+$) 389.0;

$^1$H NMR (400 Hz, DMSO-d$_6$) δ 2.71 (s, 3H, CH$_3$), 6.86 (d, J=7.2 Hz, 1H, ArH), 7.07-7.16 (m, 3H, ArH), 7.31 (d, J=8.0 Hz, 1H, ArH), 7.37 (d, J=4.0 Hz, 1H, ArH), 10.20 (s, 1H, NH), 10.57 (s, 1H, NH);

$^{13}$C NMR (100 Hz, DMSO-d$_6$) δ 16.49, 20.05, 117.51, 117.84, 119.14, 119.61, 120.37, 120.40, 120.64, 124.99, 126.24, 127.87, 129.83, 132.63, 132.71, 135.32, 138.08, 138.60. Anal. (C$_{18}$H$_{15}$Cl$_2$O$_2$S$_2$): Calcd, C, 55.31; H, 3.87; N, 7.17; S, 16.41. Found, C, 55.37; H, 3.60; N, 7.45; S, 16.27.

Embodiment 22

Preparation of Compound 61 (3,5-Dichloro-4-(2-chloro-4-nitrophenoxy)-N-(5,8-dimethyl-9H-carbazol-1-yl)benzenesulfonamide))

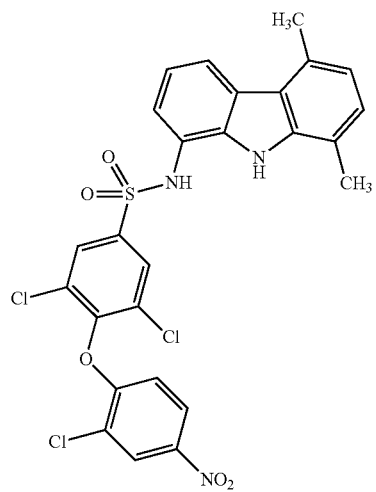

61

A mixture of 4 (1.0 g, 6.16 mmol) and 10% Pd/C (0.2 g) in methanol (30 mL) was stirred under hydrogen for 1 hour. Pd/C was removed by filtration and filtrate was evaporated in vacuo to yield oily product. To the product, CH$_2$Cl$_2$ (30 mL) and 3,5-dichloro-4-(2-chloro-4-nitrophenoxy)-benzenesulfonyl chloride (2.6 g, 6.26 mmol) were added and stirred at room temperature for 1 hour. The reaction was roughly purified by passing through silica gel packed funnel and wash with ethyl acetate. The filtrate was evaporated in vacuo and the crude product was reacted with acetonylacetone (0.7 mL, 6.62 mmol) in the presence of p-toluenesulfonic acid (1.10 g, 6.39 mmol) in EtOH (20 mL) at reflux for 3 hours. Finally, the mixture was purified with column chromatography and recrystallization in ethanol to afford white solids, compound 61 (1.85 g, 50.97%; Hex/EA=6/1, $R_f$=0.24).

mp=249° C.;
ESI (M-H+) 588.1;
$^1$H NMR (400 Hz, DMSO-$d_6$) δ 2.43 (s, 3H, $CH_3$), 2.71 (s, 3H, $CH_3$), 6.07 (d, J=8.8 Hz, 1H, ArH), 6.89 (d, J=7.2 Hz, 1H, ArH), 7.09 (d, J=7.2 Hz, 1H, ArH), 7.14 (t, J=8.0 Hz, 1H, ArH), 7.28 (d, J=7.6 Hz, 1H, ArH), 7.59 (dd, J=8.8 Hz, 2.4 Hz, 1H, ArH), 7.89 (s, 2H, ArH), 7.95 (d, J=8.0 Hz, 1H, ArH), 8.41 (d, J=2.4 Hz, 1H, ArH), 9.96 (s, 1H, NH), 10.56 (s, 1H, NH);
$^{13}$C NMR (100 Hz, DMSO-$d_6$) δ 16.49, 20.07, 113.74, 117.58, 119.35, 119.70, 120.43, 120.50, 120.84, 122.06, 124.14, 125.05, 126.42, 126.60, 128.35, 128.66, 129.97, 133.94, 138.62, 139.25, 143.13, 138.05, 155.27.

Anal. ($C_{26}H_{18}Cl_3N_3O_5S$): Calcd, C, 52.85; H, 3.07; N, 7.11; S, 5.43. Found, C, 53.10; H, 3.27; N, 7.36; S, 5.68.

Embodiment 23

Preparation of Compound 14a (1-(5,8-Dimethyl-9H-carbazol-1-yl)-3-phenylurea))

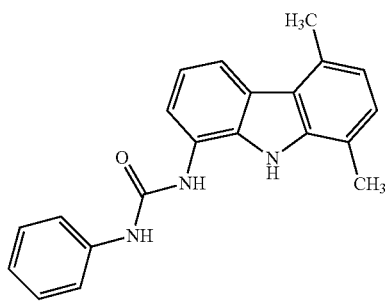

A mixture of 4 (1.0 g, 6.16 mmol) and 10% Pd/C (0.2 g) in methanol (30 mL) was stirred under hydrogen for 1 hour. Pd/C was removed by filtration and filtrate was evaporated in vacuo to yield oily product. To the product, $CH_2Cl_2$ (30 mL) and phenylisocyanate (0.7 mL, 6.42 mmol) were added and stirred at room temperature for 1 hour. The resulting suspension was filtered to give gray solid. The crude product was reacted with acetonylacetone (0.7 mL, 6.62 mmol) in the presence of p-toluenesulfonic acid (1.10 g, 6.39 mmol) in EtOH (20 mL) at reflux for 3 hours. Finally, the mixture was purified with column chromatography and recrystallization in ethanol to afford white solids, compound 14a (1.12 g, 55.17%; Hex/EA=4/1, $R_f$=0.2).

mp 300-301° C.;
ESI (M-H+) 328.8;
$^1$H NMR (400 Hz, DMSO-$d_6$) δ 2.54 (s, 3H, $CH_3$), 2.74 (s, 3H, $CH_3$), 6.89 (d, J=7.2 Hz, 1H, ArH), 6.97 (d, J=7.2 Hz, 1H, ArH), 7.08-7.16 (m, 2H), 7.29 (d, J=7.7 Hz, 2H, ArH), 7.51 (d, J=8.3 Hz, 2H, ArH), 7.60 (d, J=7.7 Hz, 1H, ArH), 7.82 (d, J=7.84 Hz, 1H, ArH), 8.53 (s, 1H, NH), 8.82 (s, 1H, NH), 10.65 (s, 1H, NH);
$^{13}$C NMR (100 Hz, DMSO-$d_6$) δ 16.81, 20.16, 117.04, 117.64, 118.31, 119.10, 120.44, 120.99, 121.79, 123.51, 124.81, 125.92, 128.79, 129.65, 131.89, 138.81, 139.92, 153.07. Anal. ($C_{21}H_{19}N_3O$·0.125$C_2H_5OH$): Calcd, C, 76.15; H, 5.94; N, 12.54. Found, C, 75.89; H, 5.88; N, 12.76.

Embodiment 24

Preparation of Compound 14b (1-(5,8-Dimethyl-9H-carbazol-1-yl)-3-(4-methoxyphenyl)urea))

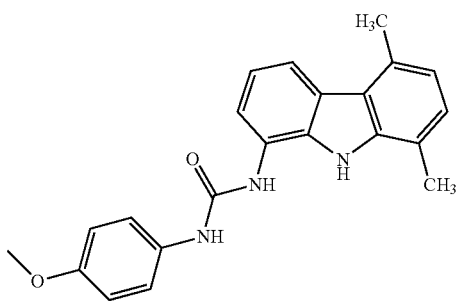

A mixture of 4 (1.0 g, 6.17 mmol) and 10% Pd/C (0.2 g) in methanol (30 mL) was stirred under hydrogen for 1 hour. Pd/C was removed by filtration and filtrate was evaporated in vacuo to yield oily product. To the product, $CH_2Cl_2$ (30 mL) and 4-methoxyphenylisocyanate (0.8 mL, 6.17 mmol) were added and stirred at room temperature for 1 hour. The resulting suspension was filtered to give gray solids. The crude product was reacted with acetonylacetone (0.7 mL, 6.62 mmol) in the presence of p-toluenesulfonic acid (1.10 g, 6.39 mmol) in EtOH (20 mL) at reflux for 3 hours. Finally, the mixture was purified with column chromatography and recrystallization in ethanol to afford white solids, compound 14b (0.83 g, 37.47%; Hex/EA=3/1, $R_f$=0.2).

mp 262-263° C.;
ESI (M-H+) 358.9;
$^1$H NMR (200 Hz, DMSO-$d_6$) δ 2.54 (s, 3H, $CH_3$), 2.74 (s, 3H, $CH_3$), 3.71 (s, 3H, $CH_3$), 6.80-6.91 (m, 3H), 7.07-7.16 (m, 2H), 7.42 (d, J=8.8 Hz, 2H, ArH), 7.60 (d, J=7.0 Hz, 1H, ArH), 7.80 (d, J=7.4 Hz, 1H, ArH), 8.50 (s, 1H, NH), 8.72 (s, 1H, NH), 10.68 (s, 1H, NH);
$^{13}$C NMR (50 Hz, DMSO-$d_6$) δ 16.85, 20.21, 55.18, 114.02, 116.73, 116.79, 117.65, 119.14, 120.13, 120.45, 121.01, 123.83, 124.78, 125.91, 129.67, 131.68, 132.97, 138.81, 153.26, 154.46, 221.88.
Anal. ($C_{22}H_{21}N_3O_2$·0.125$C_2H_5OH$): Calcd, C, 73.18; H, 6.00; N, 11.51. Found, C, 72.98; H, 5.92; N, 11.94.

Embodiment 25

Preparation of Compound 15c (N-(5,8-Dimethyl-9H-carbazol-1-yl)-N-methyl-4-methoxybenzenesulfonamide))

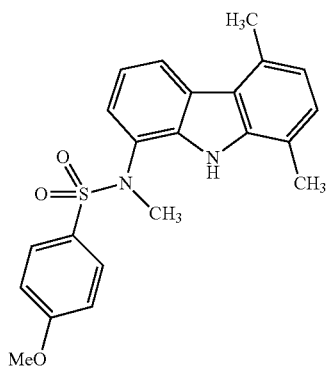

A solution of 6c (0.5 g, 1.315 mmol), KOH (1 granule) and ethanol (20 mL) was stirred at 70° C. for 15 minutes. To the solution, methyl iodide (3.0 mL) was added and stirred at 70° C. for 1 hour. The solution was purified with column chromatography to afford compound 15c (0.38 g, 73.28%; Hex/EA=6/1, $R_f$=0.3).

mp=88-89° C.;

ESI (M-H$^+$) 365.1;

$^1$H NMR (200 Hz, acetone-d$_6$) δ 2.60 (s, 3H, CH$_3$), 2.80 (s, 3H, CH$_3$), 3.29 (s, 3H, CH$_3$), 3.91 (s, 3H, CH$_3$), 6.64 (d, J=7.8 Hz, 1H, ArH), 6.92 (d, J=7.2 Hz, 1H, ArH), 7.03-7.18 (m, 4H, ArH), 7.59 (d, J=8.8 Hz, 2H, ArH), 8.10 (d, J=8.0 Hz, 1H, ArH), 10.23 (s, 1H, NH);

$^{13}$C NMR (50 Hz, acetone-d$_6$) δ 17.14, 20.65, 39.86, 56.15, 114.92, 118.87, 119.58, 119.58, 121.68, 122.82, 122.90, 126.85, 126.90, 126.97, 127.50, 129.57, 131.09, 131.14, 139.22, 140.21, 164.21.

Anal. (C$_{22}$H$_{22}$N$_2$O$_3$S): Calcd, C, 66.98; H, 5.62; N, 7.10. Found, C, 75.89; H, 5.88; N, 12.76.

Embodiment 26

Preparation of Compound 15j (N-(5,8-Dimethyl-9H-carbazol-1-yl)-N-methyl-3-trifluoromethylbenzenesulfonamide))

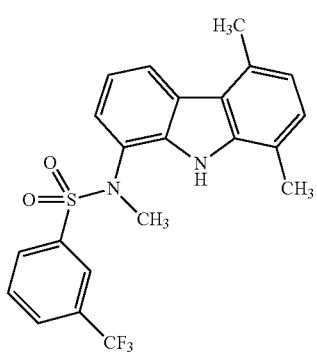

15j

A solution of 6j (0.5 g, 1.08 mmol), KOH (1 granule) and ethanol (20 mL) was stirred at 70° C. for 15 minutes. To the solution, methyl iodide (3.0 mL) was added and stirred at 70° C. for 1 hour. The solution was purified with column chromatography to afford compound 15j (0.37 g, 78.70%; Hex/EA=5/1, $R_f$=0.2).

mp=192-194° C.;

ESI (M-H$^+$) 431.1;

$^1$H NMR (200 Hz, DMSO-d$_6$) δ 2.57 (s, 3H, CH$_3$), 2.73 (s, 3H, CH$_3$), 3.33 (s, 3H, CH$_3$), 6.59 (d, J=7.8 Hz, 1H, ArH), 6.87 (d, J=7.3 Hz, 1H, ArH), 7.59 (t, J=7.8 Hz, 1H, ArH), 7.11 (d, J=7.3 Hz, 1H, ArH), 7.70-8.13 (m, 5H, ArH), 11.12 (s, 1H, NH);

$^{13}$C NMR (50 Hz, DMSO-d$_6$) δ 17.27, 20.27, 118.22, 118.55, 120.57, 120.68, 122.46, 122.53, 124.42, 124.57, 125.69, 126.76, 129.74, 130.98, 131.86, 137.83, 138.23, 139.13. Anal. (C$_{22}$H$_{19}$FN$_2$O$_2$S): Calcd, C, 61.10; H, 4.43; N, 6.48; S, 7.41. Found, C, 61.39; H, 4.49; N, 6.97; S, 7.42.

Embodiment 27

Preparation of Compound 15k (5-Chloro-thiophene-2-sulfonic acid (5,8-dimethyl-9H-carbazol-1-yl)-methyl-amide))

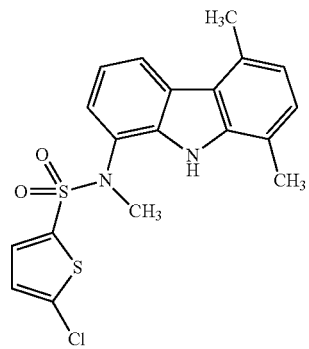

15k

A solution of 6k (0.25 g, 0.64 mmol), KOH (1 granule) and ethanol (20 mL) was stirred at 70° C. for 15 minutes. To the solution, methyl iodide (mL, mmol) was added and stirred at 70° C. for 1 hour. The solution was purified with column chromatography to afford compound 15k (0.22 g, 84.37%; Hex/EA=12/1, $R_f$=0.30).

mp=179-181° C.; ESI (M-H$^+$) 403.1; $^1$H NMR (400 Hz, DMSO-d$_6$) δ 2.57 (s, 3H, CH$_3$), 2.74 (s, 3H, CH$_3$), 3.34 (s, 3H, CH$_3$), 6.83 (d, J=7.6 Hz, 1H, ArH), 6.88 (d, J=7.2 Hz, 1H, ArH), 7.07-7.13 (m, 2H, ArH), 7.36 (d, J=4.0 Hz, 1H, ArH), 7.47 (d, J=4.0 Hz, 1H, ArH), 8.08 (d, J=7.8 Hz, 1H, ArH), 11.11 (s, 1H, NH); $^{13}$C NMR (100 Hz, DMSO-d$_6$) α 17.20, 20.18, 118.11, 118.67, 120.50, 120.55, 121.93, 122.36, 124.60, 125.55, 126.62, 128.43, 129.61, 133.12, 135.54, 137.79, 139.04. Anal. (C$_{19}$H$_{17}$ClN$_2$O$_2$S$_2$): Calcd, C, 56.36; H, 4.23; N, 6.92; S, 15.84. Found, C, 56.26; H, 4.35; N, 7.06; S, 15.49.

Embodiment 28

Preparation of Compound 16c (N-(5,8-Dimethyl-9H-carbazol-1-yl)-N-ethyl-4-methoxybenzenesulfonamide))

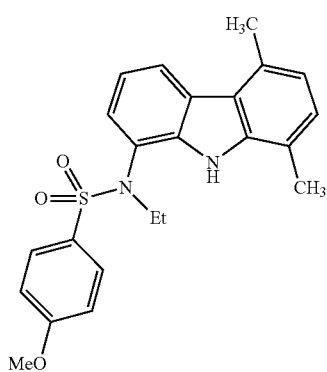

16c

A solution of 6c (0.5 g, 1.31 mmol), KOH (1 granule) and ethanol (20 mL) was stirred at 70° C. for 15 minutes. To the solution, ethyl iodide (3.0 mL) was added and stirred at 70° C. for 1 hour. The solution was purified with column chromatography to afford compound 16c (0.37 g, 68.70%; Hex/EA=6/1, $R_f$=0.36).

mp=151-152° C.;

ESI (M-H$^+$) 407.1;

$^1$H NMR (400 Hz, DMSO-d$_6$) δ 0.97 (t, J=6.8 Hz, 3H, CH$_3$), 2.58 (s, 3H, CH$_3$), 2.73 (s, 3H, CH$_3$), 3.82 (s, 3H, OCH$_3$), 6.56 (d, J=7.6 Hz, 1H, ArH), 6.87 (d, J=7.2 Hz, 1H, ArH), 7.01 (t, J=7.6 Hz, 1H, ArH), 7.06-7.11 (m, 3H, ArH), 7.58 (d, J=8.8 Hz, 2H, ArH), 8.04 (d, J=7.6 Hz, 1H, ArH), 10.91 (s, 1H, NH);

$^{13}$C NMR (100 Hz, DMSO-d$_6$) δ 13.21, 17.33, 20.22, 46.06, 55.67, 114.24, 118.09, 118.47, 120.49, 120.56, 122.06, 122.39, 123.28, 125.26, 126.57, 129.62, 129.83, 139.01, 139.42, 162.60.

Anal. (C$_{23}$H$_{24}$N$_2$O$_3$S): Calcd, C, 67.62; H, 5.92; N, 6.86. Found, C, 67.40; H, 6.18; N, 6.55.

Embodiment 29

Preparation of Compound 17c (N-(5,8-Dimethyl-9H-carbazol-1-yl)-N-propyl-4-methoxybenzenesulfonamide))

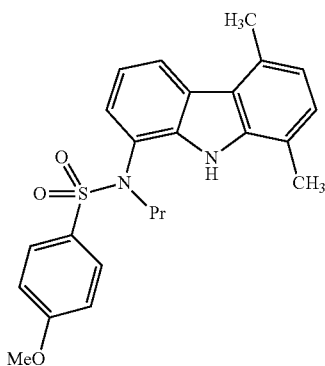

17c

A solution of 6c (0.5 g, 1.31 mmol), KOH (1 granule) and ethanol (20 mL) was stirred at 70° C. for 15 minutes. To the solution, bromopropane (2.0 mL) was added and stirred at 70° C. for 1 hour. The solution was purified with column chromatography to afford compound 17c (0.28 g, 50.38%; Hex/EA=8/1, $R_f$=0.44).

mp=60-62° C.;

ESI (M-H$^+$) 421.1;

$^1$H NMR (400 Hz, DMSO-d$_6$) δ 0.79 (t, J=7.4 Hz, 3H, CH$_3$), 2.58 (s, 3H, CH$_3$), 2.73 (s, 3H, CH$_3$), 3.35 (s, 2H, CH$_2$), 3.81 (s, 3H, OCH$_3$), 6.60 (d, J=7.6 Hz, 1H, ArH), 6.87 (d, J=7.3 Hz, 1H, ArH), 7.01 (t, J=7.7 Hz, 1H, ArH), 7.09-7.11 (m, 3H, ArH), 7.57 (d, J=8.8 Hz, 2H, ArH), 8.04 (d, J=7.8 Hz, 1H, ArH), 10.76 (s, 1H, NH);

$^{13}$C NMR (100 Hz, DMSO-d$_6$) δ 11.07, 17.28, 20.21, 21.12, 52.89, 55.64, 114.21, 118.06, 118.51, 120.52, 120.56, 121.99, 122.89, 123.35, 125.33, 126.58, 129.60, 129.69, 129.85, 138.97, 139.05, 162.60.

Anal. (C$_{24}$H$_{26}$N$_2$O$_3$S): Calcd, C, 68.22; H, 6.20; N, 6.63; S, 7.59. Found, C, 68.43; H, 6.05; N, 6.66; S, 7.26.

Embodiment 30

Preparation of Compound 18c (N-(5,8-Dimethyl-9H-carbazol-1-yl)-N-isopropyl-4-methoxybenzenesulfonamide))

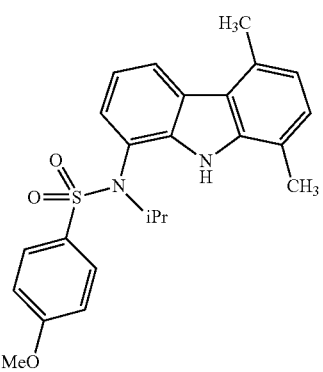

18c

A solution of GM-119 (0.5 g, 1.31 mmol), KOH (1 granule) and ethanol (20 mL) was stirred at 70° C. for 15 minutes. To the solution, 2-bromopropane (3.0 mL) was added and stirred at 70° C. for 1 hour. The solution was purified with column chromatography to afford compound 4c (0.22 g, 39.69%; Hex/EA=8/1, $R_f$=0.39).

mp=222-224° C.;

ESI (M-H$^+$) 421.1;

$^1$H NMR (400 Hz, acetone-d$_6$) δ 1.12 (t, J=6.6 Hz, 6H, CH$_3$), 2.56 (s, 3H, CH$_3$), 2.81 (s, 3H, CH$_3$), 2.85 (s, 2H, CH$_2$), 3.87 (s, 3H, OCH$_3$), 4.78 (m, 1H, CH), 6.79 (d, J=7.6 Hz, 1H, ArH), 6.92 (d, J=7.3 Hz, 1H, ArH), 7.03-7.15 (m, 4H, ArH), 7.66 (d, J=8.9 Hz, 2H, ArH), 8.18 (d, J=7.9 Hz, 1H, ArH), 10.02 (s, 1H, NH);

$^{13}$C NMR (100 Hz, acetone-d$_6$) δ 17.15, 20.64, 21.86, 22.20, 23.32, 53.17, 56.09, 114.83, 118.77, 119.18, 120.27, 121.74, 122.06, 123.69, 126.90, 127.49, 128.51, 130.73, 131.08, 133.77, 140.06, 141.98, 163.87. Anal. (C$_{24}$H$_{26}$N$_2$O$_3$S): Calcd, C, 68.22; H, 6.20; N, 6.63; S, 7.59. Found, C, 68.12; H, 6.43; N, 6.45; S, 7.25.

Embodiment 31

Preparation of Compound 20 (1-Nitro-9H-carbazole))

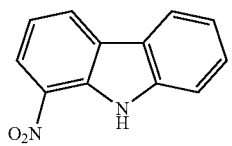

20

A mixture of 19 (1 g, 5.98 mmol) and acetic acid (10 mL) was stirred at 70° C. for 20 minutes. To the mixture, nitric acid (0.3 mL) was added and stirred at 70° C. for 1 hour. The reaction was quenched by water and filtered to afford yellow solids. The crude product was purified with column chromatography to afford yellow solids, compound 20 (0.45 g, 35.45%; Hex/EA=12/1, $R_f$=0.5).

mp 195-196° C.;

ESI (M-H⁺) 211.0;

¹H NMR (400 Hz, DMSO-d₆) δ 7.27-7.37 (m, 2H, ArH), 7.51 (t, J=7.2 Hz, 1H, ArH), 7.75 (d, J=8.0 Hz, 1H, ArH), 8.23 (d, J=7.6 Hz, 1H, ArH), 8.30 (d, J=7.7 Hz, 1H, ArH), 8.60 (d, J=7.2 Hz, 1H, ArH), 12.16 (s, 1H, NH);

¹³C NMR (100 Hz, DMSO-d₆) δ 112.64, 118.36, 120.65, 120.70, 121.53, 121.72, 127.14, 127.35, 128.08, 131.70, 132.93, 140.68.

Anal. ($C_{12}H_8N_2O_2$): Calcd, C, 67.92; H, 3.80; N, 13.20. Found, C, 67.94; H, 3.95; N, 13.21.

Embodiment 32

Preparation of Compound 21a (N-(9H-Carbazol-1-yl)-4-methoxybenzenesulfonamide))

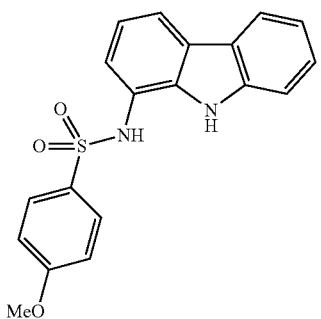

21a

A solution of 20 (0.5 g, 2.35 mmol), Pd/C (0.1 g) and methanol (30 mL) was stirred under hydrogen gas at the ambient temperature for 1 hour. The Pd/C solid was removed with filtration and the solvent was evaporated in vacuo to furnish oily product. To the crude product, 4-methoxybenzenesulfony chloride (0.5 g, 2.42 mmol), triethylamine (1.0 mL) and ethyl acetate (50 mL) were added and stirred at 50° C. for 2 hours. The mixture was purified with column chromatography to afford white solids, compound 21a (0.43 g, 53.50%; Hex/EA=3/1, $R_f$=0.30).

mp 204-206° C.;

ESI (M-H⁺) 351.0;

¹H NMR (400 Hz, DMSO-d₆) δ 3.74 (s, 3H, OCH₃), 6.90-7.02 (m, 4H, ArH), 7.14 (t, J=7.2 Hz, 1H, ArH), 7.38 (t, J=7.6 Hz, 1H, ArH), 7.57 (d, J=8.0 Hz, 1H, ArH), 7.67 (d, J=8.8 Hz, 1H, ArH), 7.88 (d, J=7.6 Hz, 1H, ArH), 8.05 (d, J=7.6 Hz, 1H, ArH), 9.80 (s, 1H, NH), 10.94 (s, 1H, NH);

¹³C NMR (100 Hz, DMSO-d₆) δ 55.58, 111.50, 114.22, 117.77, 118.64, 118.88, 119.91, 120.20, 121.00, 122.27, 123.99, 125.85, 129.12, 131.14, 134.59, 139.49, 162.40.

Anal. ($C_{19}H_{16}N_2O_3S$): Calcd, C, 64.76; H, 4.58; N, 7.95; S, 9.10. Found, C, 64.79; H, 4.75; N, 7.88; S, 8.47.

Embodiment 33

Preparation of Compound 21b (N-(9H-Carbazol-1-yl)-3-trifluoromethylbenzenesulfonamide))

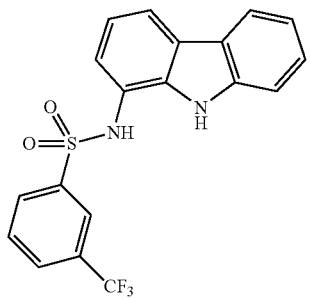

21b

A solution of 20 (0.5 g, 2.35 mmol), Pd/C (0.1 g) and methanol (30 mL) was stirred under hydrogen gas at the ambient temperature for 1 hour. The Pd/C solid was removed with filtration and the solvent was evaporated in vacuo to furnish oily product. To the crude product, 3-trifluoromethylbenzenesulfonyl chloride (0.6 g, 2.45 mmol), triethylamine (1.0 mL) and ethyl acetate (50 mL) were added and stirred at 50° C. for 2 hours. The mixture was purified with column chromatography to afford white solids, compound 21b (0.54 g, 58.59%; Hex/EA=8/1, $R_f$=0.21).

mp 188-190° C.;

ESI (M-H⁺) 389.0;

¹H NMR (400 Hz, DMSO-d₆) δ 6.75 (d, J=7.6 Hz, 1H, ArH), 6.96 (t, J=7.7 Hz, 1H, ArH), 7.14 (t, J=7.5 Hz, 1H, ArH), 7.38 (t, J=7.7 Hz, 1H, ArH), 7.54 (d, J=8.1 Hz, 1H, ArH), 7.74 (d, J=7.7 Hz, 1H, ArH), 7.94-7.79 (m, 4H, ArH), 8.06 (d, J=7.7 Hz, 1H, ArH), 10.08 (s, 1H, NH), 11.02 (s, 1H, NH);

¹³C NMR (100 Hz, DMSO-d₆) δ 111.51, 118.61, 118.93, 119.02, 119.82, 120.32, 121.49, 122.22, 123.60, 124.30, 124.73, 126.07, 129.66, 129.89, 130.79, 131.01, 135.65, 139.69, 140.62.

Anal. ($C_{19}H_{13}F_3N_2O_2S$): Calcd, C, 58.46; H, 3.36; N, 7.18; F, 14.60; S, 8.21. Found, C, 72.98; H, 5.92; N, 11.94.

[Evaluation of the Pharmacological Activity]

Human Bladder Cancer TSGH cells, Human hepatoblastoma HepG2 cells, Human colorectal adenocarcinoma HT-29 cells, human nasopharyngeal carcinoma KB cells, Human gastric adenocarcinoma AGS cells, Human breast carcinoma MCF-7 cells, lung carcinoma A549 cells, and Human prostate carcinoma PC-3 cells were used in the preliminary cytotoxicity assays of the benzenesulfonamide derivatives of the present invention, and the inhibition activity against the tumor cells was evaluated.

[MTT Assay]

All cell lines were maintained in RPMI 1640 supplied with 10% fetal bovine serum and maintained in a humidified chamber at 37° C. containing 5% $CO_2$. Then, all cell lines were treated with compounds for 72 hr and subsequently incubated with 0.4 mg/mL of MTT at 37° C. for 2 hr. The medium was removed, and DMSO was added to dissolve MTT precipitate. Cell proliferation was determined by measuring the optical density at 540 nm using a Thermomax microplate reader (Molecular Devices, Sunnyvale, Calif.), and the $IC_{50}$ values of the benzenesulfonamide derivatives of the present invention were calculated.

[SRB Assay]

All cell lines were maintained in RPMI 1640 supplied with 10% fetal bovine serum into 96-well microtiter plates and maintained in a humidified chamber at 37° C. containing 5% $CO_2$. After 24 hr, cell lines in partial wells were fixed in situ with 10% trichloroacetic acid (TCA) to represent a measurement at the time of drug addition ($T_0$). Then, cell lines in other wells were incubated with the benzenesulfonamide derivatives of the present invention for an additional 48 hr, and fixed in situ with 10% TCA to represent a measurement at the time of stopping reaction ($T_x$). After rinsing the plates with PBS and air-drying, 0.4% sulforhodamine B solution (weight per volume in 1% acetic acid) was added to each well and the plates were incubated for 10 min at room temperature. Unbound sulforhodamine B was removed with 1% acetic acid and the plates were air-dried. Cells bound with sulforhodamine B was subsequently solubilized with 10 mM Tris base (Trizma; Sigma). Cell proliferation was determined by measuring the optical density at 515 nm using a Thermomax microplate reader (Molecular Devices, Sunnyvale, Calif.). The half-inhibition concention ($GI_{50}$) of the benzenesulfonamide derivatives of the present invention was obtained from the detected optical density.

TABLE 1

Results of MTT assay

| Compound | $IC_{50}$ (μM) | | | |
|---|---|---|---|---|
| | TSGH | HepaG2 | HT-29 | KB |
| 5a | 7.5 | 44.7 | 51.9 | >20 (30%)[a] |
| 5b | 9.4 | 7.9 | 7.9 | >20 (39%)[a] |
| 5c | 2.4 | 1.9 | 1.7 | 3.4 |
| 5d | 35.6 | 14.0 | 19.8 | 20.0 |
| 5e | 95.6 | 46.9 | 113.3 | >20 (14%)[a] |
| 5g | 37.5 | 39.2 | 65.9 | >20 (12%)[a] |
| 5h | 125.0 | 87.8 | 126.2 | >20 (13%)[a] |
| 6a | 160.0 | 66.7 | 140.9 | >20 (32%)[a] |
| 6b | 2.1 | 1.7 | 1.1 | 2.5 |
| 6c | 0.5 | 0.4 | 0.4 | 0.8 |
| 6d | 90.0 | 34.4 | 81.6 | >20 (46%)[a] |
| 6e | 40.6 | 19.8 | 17.6 | >20 (9%)[a] |
| 6f | 39.0 | 16.6 | 18.7 | >20 (34%)[a] |
| 6g | 80.7 | 138.8 | 123.8 | 19.1 |
| 6h | 37.2 | 21.0 | 17.0 | >20 (24%)[a] |
| 7a | 3.6 | 9.1 | 5.9 | 4.5 |
| 7b | 16.0 | 30.8 | 17.9 | >20 (35%)[a] |
| 7c | 14.2 | 28.4 | 13.8 | 15.3 |

[a]Percentage of tumor cells inhibited by 20 μM of the benzenesulfonamide derivatives

TABLE 2

Results of SRB assay

| Com-pound | HT-29 | | AGS | | MCF-7 | |
|---|---|---|---|---|---|---|
| | $GI_{50}$ (μM) | $IC_{50}$ (μM) | $GI_{50}$ (μM) | $IC_{50}$ (μM) | $GI_{50}$ (μM) | $IC_{50}$ (μM) |
| 6c | 0.32 | 9.0 | 0.6 | 1.0 | 0.63 | >10 |
| 17c | 0.3 | 0.8 | 0.6 | >10 | 6.1 | >10 |
| 18c | 0.2 | 0.7 | 0.5 | >10 | 9.5 | >10 |
| 6k | 2.1 | 5.6 | 6.7 | >10 | >10 | >10 |
| 15k | 0.3 | 3.9 | 7.5 | >10 | >10 | >10 |
| 21a | 0.03 | 0.07 | 0.01 | 0.07 | 0.07 | 4.4 |
| 15c | >10 | >10 | >10 | >10 | >10 | >10 |
| 6j | >10 | >10 | >10 | >10 | >10 | >10 |
| 21b | >10 | >10 | >10 | >10 | >10 | >10 |
| 15j | 5.6 | 10 | 7.8 | >10 | 7.8 | >10 |
| 16c | 0.05 | 0.3 | 0.4 | 1.0 | 0.4 | 0.8 |

TABLE 3

Results of SRB assay

| Com-pound | A549 | | HepG2 | | PC-3 | |
|---|---|---|---|---|---|---|
| | $GI_{50}$ (μM) | $IC_{50}$ (μM) | $GI_{50}$ (μM) | $IC_{50}$ (μM) | $GI_{50}$ (μM) | $IC_{50}$ (μM) |
| 6c | 0.28 | 10 | 0.07 | 1.0 | 0.5 | 1.1 |
| 17c | 5.9 | 10 | 0.8 | 1.9 | 3.5 | 8.6 |
| 18c | 7.8 | >10 | 0.5 | 1.6 | 4.0 | 9.4 |
| 6k | 6.5 | 10 | 1.3 | 2.7 | 4.6 | >10 |
| 15k | 8.1 | >10 | 0.7 | 1.6 | 7.0 | >10 |
| 21a | 0.9 | 1.7 | 0.04 | 0.08 | 0.2 | >10 |
| 15c | >10 | >10 | >10 | >10 | >10 | >10 |
| 6j | >10 | >10 | >10 | >10 | >10 | >10 |
| 21b | >10 | >10 | >10 | >10 | >10 | >10 |
| 15j | >10 | >10 | >10 | >10 | >10 | >10 |
| 16c | 0.4 | >10 | 0.04 | 0.08 | 0.06 | 0.3 |

TABLE 4

Antiproliferative activity of the Compound 6c

| | Tumor cell lines | $IC_{50}$ (μM) MTT assay | $GI_{50}$ (μM) SRB assay |
|---|---|---|---|
| A549 | non-small cell lung cancer | 1.12 | 0.28 |
| CL1-5 | non-small cell lung cancer | ND[b] | 0.26 |
| H1299 | non-small cell lung cancer | ND[b] | 0.46 |
| AGS | Stomach cancer | 1.40 | 0.60 |
| HeLa | Cervical cancer | 0.60 | 0.19 |
| HepG2 | Liver cancer | 0.40 | 0.07 |
| HT-29 | Colon cancer | 0.40 | 0.32 |
| COLO-205 | Colon cancer | 0.05 | ND[b] |
| MCF-7 | Breast cancer | 0.24 | 0.63 |
| MCF-7/ADR[a] | Breast cancer | ND[b] | 0.39 |
| PC-3 | Prostate cancer | 0.24 | 0.61 |
| WI-38 | Normal lung fibroblast cancer | >10 | ND[b] |
| WSI | Normal skin fibroblast cancer | >10 | ND[b] |

[a]MCF-7/ADR: multidrug-resistant breast cancer
[b]ND: Not determined

According to the results shown in Table. 1, the compounds 6a-6h have higher inhibitory activity against the tumor cells than the compounds 5a-5h. For example, the $IC_{50}$ values of the compound 6b against TSGH, HepaG2, HT-29, and KB cancer cells are respectively 2.1, 1.7, 1.1 and 2.5 µM, and the $IC_{50}$ values of the compound 5b are respectively 9.4, 7.9, 7.9, and >20 µM. Among all the benzenesulfonamide derivatives of the present invention, the compound 6c with a methoxy group at the $4^{th}$ position of the benzene ring has the best inhibition activity, and the $IC_{50}$ values of the compound 6c against TSGH, HepaG2, HT-29, and KB cancer cells are respectively 0.5, 0.4, 0.4 and 0.8 µM. However, according to the paper published by Owa et al. (*J. Med. Chem.* 1999, 42, 3789-3799), the $IC_{50}$ values of E7070 (Eisai Co., Ltd.) against KB cells, colon 38 cells, and P388 murine leukemia cells are respectively 11.4, 0.3 and 1.2 µM. Hence, the compound 6c of the present invention has higher inhibitory activity against KB cells than E7070. In addition, the compounds 6b-6g with substitution groups at the para-position have better inhibitory activity than the compound 6a without any substituted groups. Hence, the substitution group at the para-position can increase the inhibition activity against tumor cells.

In addition, the results also show that the compounds 7a-7c have the inhibitory activity against tumor cells, and the inhibitory activity of the compounds 7a and 7c is higher than that of the compound 5d. For example, the $IC_{50}$ values of the compound 7a against TSGH, HepaG2, HT-29, and KB cancer cells are respectively 3.6, 9.1, 5.9 and 4.5 µM, and the $IC_{50}$ values of the compound 5d are respectively 35.6, 14, 19.8 and 20 µM. Hence, the compounds 7a-7c have the potential for the inhibition of the growth of the tumor cells.

According to the results shown in Tables 1-4, the benzenesulfonamide derivatives of the present invention have the ability to inhibit the growth of the tumor cells, and the compound 6c has the highest inhibitory activity. In addition, the benzenesulfonamide derivatives of the present invention can cause the cell death through inhibiting cell cycle progression, so these compounds can be used for the treatment on solid tumors.

Next, the inhibitory activity against tumor cells of the benzenesulfonamide derivative of the present invention is evaluated by in vitro and in vivo assays. Hereafter, the compound 6c of the present invention is called GM 119.

In Vitro Migration Assay

Lung carcinoma A549 cells (BCRC 60074; BCRC) were maintained in RPMI 1640 supplied with 10% fetal bovine serum and maintained in a humidified chamber at 37° C. containing 5% $CO_2$. All the cell lines were developed for two generations every week.

In the in vitro migration assay, a scratch was mechanically made on the monolayer of cells to form a line-shaped scratch with cytological exfoliation. The scratch may lead the edge of the cell monolayer to close.

When the monolayered A549 cells were saturated, a scratch was made using a 200-µL tip directly on the monolayer of the A549 cells. Cells were then treated with GM119 with a concentration of 0, 0.5, or 10 µM. After incubation for 18 hr, all the migrations were tracked with a microscope. The images showed that the inhibition on the migration of the A549 cells was greater as the concentration of the GM119 was increased.

In addition, 25 µg of cell extraction of the A549 treated with GM 119 with different concentration was observed by western blotting. Sample was separated by SDS-PAGE, transferred, and visualized with the antibodies of anti-p53, anti-p-p53, and anti-actin.

In Vitro Tube Formation Assay for Evaluating the Capillary Formation

At day 1, HUVECs (human umbilical vein endothelial cells) cocultured with human fibroblasts were incubated in optimized medium and maintained in a humidified chamber at 37° C. containing 5% $CO_2$. After 1 day, recombinant human VEGF (25 ng/mL) was added to the medium as a positive control, and VEGF (25 ng/mL) combined with suramin (2 M) was used as a negative control. The cells were stimulated with VEGF (25 ng/mL) without or with GM119 (0.1, 1 or 10 µM). The media were replaced at days 3, 6, and 8. At day 11, the tube-like structures of the umbilical vein endothelial cells were observed by an anti-human CD31 antibody (Kurabo, Tokyo, Japan), and the area of the tube-like structures was analyzed.

After the analysis of the phase-contrast microscope, it can be found that GM119 can inhibit the formation of the tube-like structures of the umbilical vein endothelial cells induced by VEGF. In addition, compared with the inhibition results of 10 µM GM119 with 10 µM suramin, it can be found that the inhibition activity of GM119 is almost equivalent to that of suramin.

Evaluation of the Effect of the Benzenesulfonamide Derivative in the Murine Mammary Carcinoma 4T1 Model with Chemiluminescence Imaging The murine mammary carcinoma cell line 4T1-Luc cells stably expressing the firefly luciferase gene under the selection of G418 was cultured in RPMI containing 10% fetal calf serum. The cells were maintained at 37° C. with 5% $CO_2$ in air and subcultured twice weekly.

Each well of 96-well plates was seeded with 2,500 or 5,000 tumor cells, and the tumor cells were incubated in medium with 10% fetal bovine serum or without serum. The tumor cells were treated with 0, 0.01, 0.1, 1, or 10 µM of GM119 for 48 hr. Then, the tumor cells were fixed with 10% of trichloroacetic acid, washed with water, stained with sulforhodamine B. Then, the sample was washed with 1% of acetic acid, and Tris buffer was added into the sample. The absorption of the sample was determined at 515 nm with a Thermomax microplate reader, and repeated for 4 times. The absorption of the cells without drug treatment served as 100% survival, and the survival was calculated and represented by average±standard deviation %.

As shown in FIG. 1, in the medium with or without serum, the growth of the 4T1 cells can be inhibited by use of 0.01 µM of GM119. In addition, when the concentration of GM119 is 10 µM, the inhibition of the 4T1 cells is apparent.

In Vitro Analysis on Cell Morphology

After the 4T1-Luc cells were treated with GM119, a phase-contrast microscope was used to observe the cell morphology of the 4T1-Luc cells. Cover glasses were placed in 6-well plates, and each well was seeded with 50,000 tumor cells. The tumor cells were developed in medium with 10% fetal bovine serum, and then treated with 0, 0.01, 0.1, 1, or 10 µM of GM119 for 48 hr. The cells were stained with Giemsa Stain solution (0.38 g of Giemsa powder, 15% of methanol, and 5% of glycerol). After the cells were washed, dried, and sealed, the images of the cells were photographed with a phase-contrast microscope.

From the images obtained under microscope analysis, the growth of the 4T1 cells can be inhibited by use of 0.01 µM of GM119. In addition, when the concentration of GM119 is 10 µM, the inhibition of the 4T1 cells is apparent.

Western Blot Analysis

After the 4T1-Luc cells were treated with GM119 (0, 0.01, 0.1, 1, or 10 µM) for 36 hr, the cells were collected with a centrifuge. Then, the collected cells were disrupted on ice with ultra-sonication for 15 sec. After centrifugation, the upper layer of the cell lysate was collected to obtain a cell extract. The protein concentration was analyzed with a Bradford dye-binding method (BioRad, U.S.A). 25 μg of the cell extract was separated by SDS-PAGE, transferred, and visualized with the antibodies of anti-p53, anti-p-p53, and anti-actin.

In Vivo Evaluation of GM119

GM119 (25 mg/kg) was applied to a mouse implanted with 4T1-Luc cells for a short time, and then Taxol (10 mg/kg) was applied thereto to observe the effect of GM119 on the 4T1-Luc cells.

A suspension of 4T1-Luc cells in matrigel was injected into the breast adipocyte to obtain mice implanted with luciferase tumor cells. The size of the tumor cells was observed with a Night OWL optic every day before applying GM119. When the size of the tumor cells was achieved to 200-500 mm³, the mice were divided into 2 groups, and the number of the mice in each group is ≧5. Then, 0 or 25 mg/kg of GM119 was abdominal-injected into the mice for 5 days, wherein GM119 was dissolved in cremophor, and the volume of injection to each mouse is 50 μl. Then, 0 or 10 mg/kg of Taxol was abdominal-injected into the mice for every 2 days until death of the mice. The weight and the number of the mice were recorded every day to analyze the change on the weight and the survival time of the mice. After the drugs were applied to the mice, the size of the tumor cells in the mice was evaluated with bioluminescence every two days.

Figure 2:
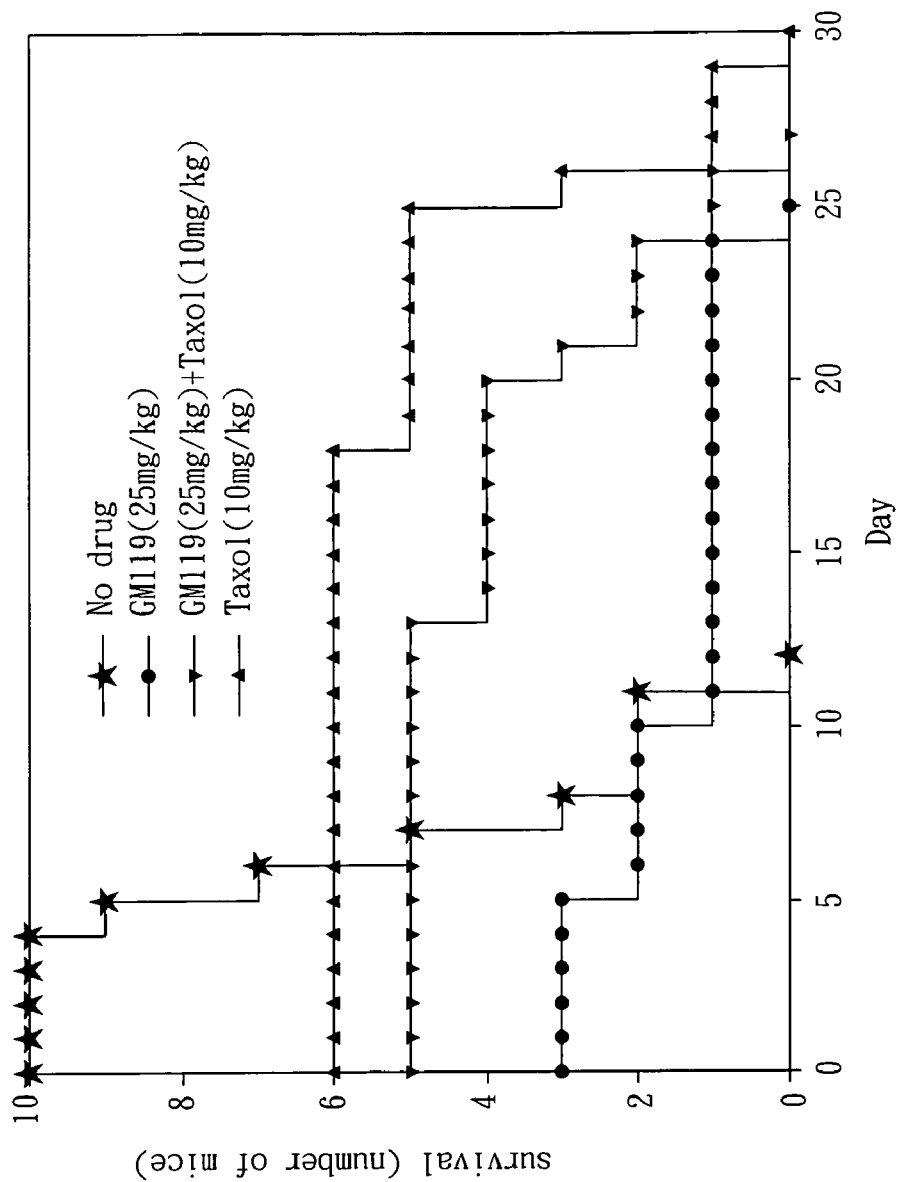
FIG. 2 is a result showing the survival time of mice treated with the benzenesulfonamide derivative of the present invention for a short time.

FIG. 2 is the result showing the survival time of mice treated with drugs for a short time. As shown in FIG. 2, the survival of the mice can be greatly increased by use of GM119 alone or combined with Taxol, as the same result by use of Taxol alone. In addition, the results of bioluminescence show that the growth of the tumor cells can be inhibited by use of GM119, Taxol, or a combination thereof.

GM119 (25 mg/kg) and Taxol (10 mg/kg) were simultaneously applied to a mouse implanted with 4T1-Luc cells for a long time to observe the effect of GM119 on the 4T1-Luc cells.

A suspension of 4T1-Luc cells in matrigel was injected into the breast adipocyte to obtain mice implanted with luciferase tumor cells. The size of the tumor cells was observed with a Night OWL optic every day before applying GM119. When the size of the tumor cells was achieved to 200-500 mm³, the mice were divided into 2 groups, and the number of the mice in each group is ≧5. Then, 0/0, 0/25, 10/23, or 10/0 mg/kg of Taxol/GM119 was abdominal-injected into the mice every two days until death of the mice, wherein GM119 and Taxol were dissolved in cremophor, and the volume of injection to each mouse is 50 μl. The weight and the number of the mice were recorded every day to analyze the change on the weight and the survival time of the mice. After the drugs were applied to the mice, the size of the tumor cells in the mice was evaluated with bioluminescence every two days.

Figure 3:
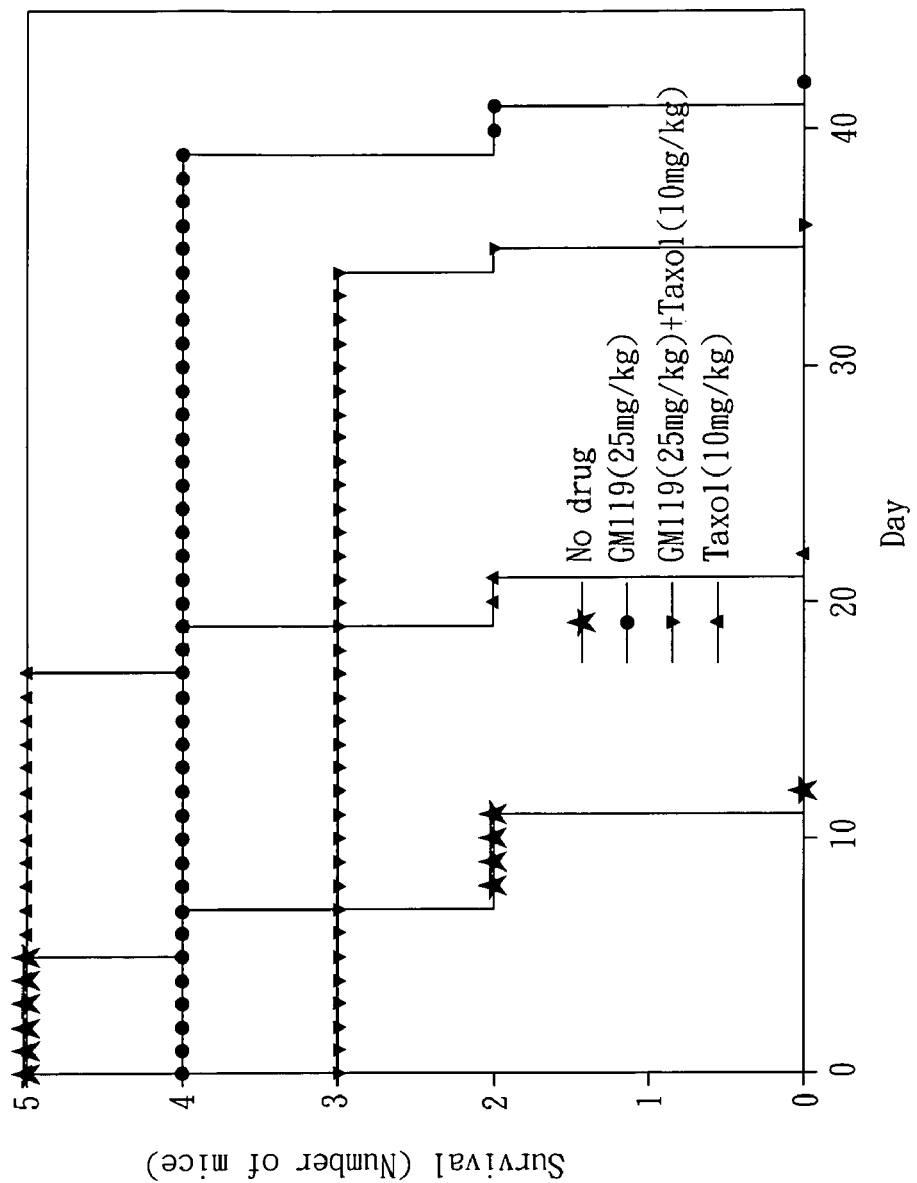
FIG. 3 is a result showing the survival time of mice treated with the benzenesulfonamide derivative of the present invention for a long time.

FIG. 3 is the result showing the survival time of mice treated with drugs for a long time. As shown in FIG. 3, the survival of the mice can be increased when Taxol was applied for a long time, but the survival can be further increased when Taxol and GM119 were applied at the same time. In addition, when GM119 alone was applied for a long time, the survival time of the mice is the longest. Furthermore, the results of bioluminescence show that the growth of the tumor cells can be inhibited by use of GM119, Taxol, or a combination thereof.

Although the present invention has been explained in relation to its preferred embodiment, it is to be understood that many other possible modifications and variations can be made without departing from the scope of the invention as hereinafter claimed.

What is claimed is:

1. A benzenesulfonamide derivative, represented by the following formula (I):

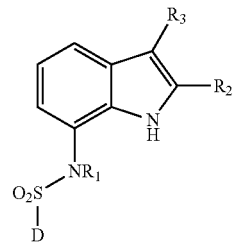

wherein,
$R_1$ is H, or $C_{1-6}$ alkyl;
$R_2$ is H, and $R_3$ is

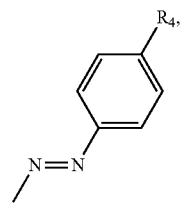

or $R_2$ and $R_3$ bond together to form

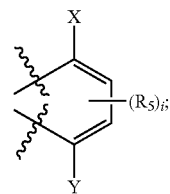

D is

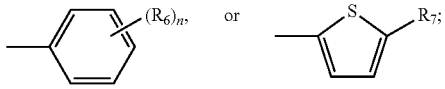

$R_4$ is H, or nitro;
X, Y, and each $R_5$ are each independently $C_{1-6}$ alkyl;
each $R_6$ is independently H, halogen, $C_{1-6}$ alkyl, $C_{1-6}$ alkoxy, $C_{1-6}$ alkyl substituted with halogen, $C_{1-6}$ alkoxy substituted with halogen, nitro, —$NR_8R_9$, or —$SO_2NR_{10}R_{11}$;
$R_7$ is H, or halogen;
$R_8$, $R_9$, $R_{10}$, and $R_{11}$ are each independently H, or $C_{1-6}$ alkyl; and
is 0, 1, or 2; and
n is 0, 1, 2, or 3.

2. The benzenesulfonamide derivative as claimed in claim 1, wherein $R_8$, and $R_9$ are H.

3. The benzenesulfonamide derivative as claimed in claim 1, wherein $R_{10}$, and $R_{11}$ are H.

4. The benzenesulfonamide derivative as claimed in claim 1, wherein $R_1$ is H, or $C_{1-3}$ alkyl, D is

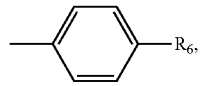

and $R_6$ is H, halogen, $C_{1-6}$ alkyl, $C_{1-6}$ alkoxy, nitro, —$NH_2$, or —$SO_2NH_2$.

5. The benzenesulfonamide derivative as claimed in claim 4, wherein $R_6$ is H, Cl, methyl, methoxy, nitro, —$NH_2$, or —$SO_2NH_2$.

6. The benzenesulfonamide derivative as claimed in claim 4, wherein $R_2$ and $R_3$ bond together to form

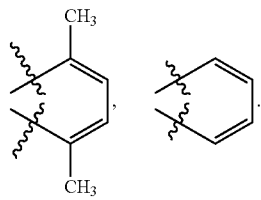

7. The benzenesulfonamide derivative as claimed in claim 1, wherein, $R_1$ is H, or $C_{1-3}$ alkyl, D is

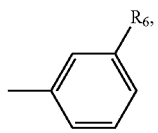

and $R_6$ is H, $C_{1-6}$ alkyl substituted with halogen, or $C_{1-6}$ alkoxy substituted with halogen.

8. The benzenesulfonamide derivative as claimed in claim 7, wherein $R_6$ is —$CF_3$.

9. The benzenesulfonamide derivative as claimed in claim 7, wherein $R_2$ and $R_3$ bond together to form

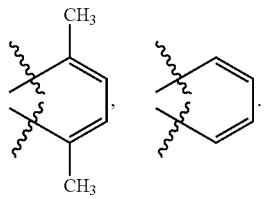

10. The benzenesulfonamide derivative as claimed in claim 1, wherein $R_1$ is H, D is

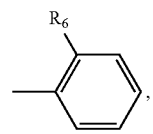

and $R_6$ is H, halogen, $C_{1-6}$ alkyl, $C_{1-6}$ alkoxy, nitro, —$NH_2$, or —$SO_2NH_2$.

11. The benzenesulfonamide derivative as claimed in claim 10, wherein $R_6$ is nitro.

12. The benzenesulfonamide derivative as claimed in claim 10, wherein $R_2$ and $R_3$ bond together to form

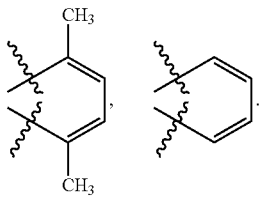

13. The benzenesulfonamide derivative as claimed in claim 1, wherein $R_1$ is H, or $C_{1-3}$ alkyl, D is

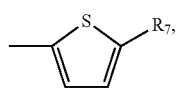

and $R_7$ is H, or halogen.

14. The benzenesulfonamide derivative as claimed in claim 13, wherein $R_1$ is H, or methyl, and $R_7$ is Cl.

15. The benzenesulfonamide derivative as claimed in claim 13, wherein $R_2$ and $R_3$ bond together to form

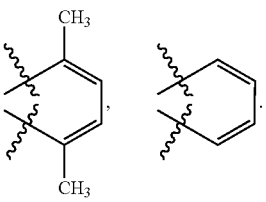

16. The benzenesulfonamide derivative as claimed in claim 1, wherein the benzenesulfonamide derivative is used as a cell cycle inhibitor.

17. The benzenesulfonamide derivative as claimed in claim 1, wherein the benzenesulfonamide derivative inhibits the growth of gastric carcinoma cells, colon carcinoma cells, and nasopharyngeal carcinoma cells.

18. A pharmaceutical composition used as a cell-cycle inhibitor, comprising an effective amount of a benzenesulfonamide derivative represented by the following formula (I),

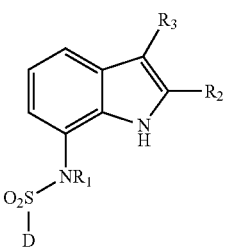

wherein,
$R_1$ is H, or $C_{1-6}$ alkyl;
$R_2$ is H, and $R_3$ is

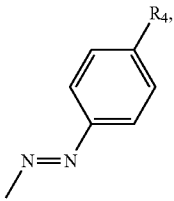

or $R_2$ and $R_3$ bond together to form

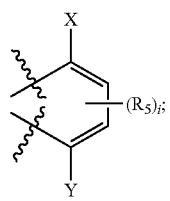

D is

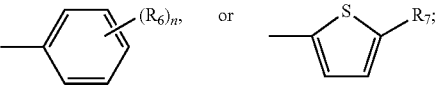

$R_4$ is H, or nitro;
X, Y, and each $R_5$ are each independently $C_{1-6}$ alkyl;
each $R_6$ is independently H, halogen, $C_{1-6}$ alkyl, $C_{1-6}$ alkoxy, $C_{1-6}$ alkyl substituted with halogen, $C_{1-6}$ alkoxy substituted with halogen, nitro, —$NR_8R_9$, or —$SO_2NR_{10}R_{11}$;
$R_7$ is H, or halogen;
$R_8$, $R_9$, $R_{10}$, and $R_{11}$ are each independently H, or $C_{1-6}$ alkyl; and
i is 0, 1, or 2; and
n is 0, 1, 2, or 3.

* * * * *